United States Patent
Day et al.

(10) Patent No.: US 9,542,861 B2
(45) Date of Patent: Jan. 10, 2017

(54) MEDICAL TRAINING KITS AND METHODS TO SIMULATE TREATMENT OF UNCONTROLLED HEMORRHAGE

(71) Applicant: LUNA INNOVATIONS INCORPORATED, Roanoke, VA (US)

(72) Inventors: Bradford L. Day, Palmyra, VA (US); Michael J. Danilich, Charlottesville, VA (US)

(73) Assignee: LUNA INNOVATIONS INCORPORATED, Roanoke, VA (US)

( * ) Notice: Subject to any disclaimer, the term of this patent is extended or adjusted under 35 U.S.C. 154(b) by 0 days.

(21) Appl. No.: 14/380,276

(22) PCT Filed: Feb. 22, 2013

(86) PCT No.: PCT/US2013/027329
§ 371 (c)(1),
(2) Date: Aug. 21, 2014

(87) PCT Pub. No.: WO2013/126707
PCT Pub. Date: Aug. 29, 2013

(65) Prior Publication Data
US 2015/0037774 A1  Feb. 5, 2015

Related U.S. Application Data

(63) Continuation of application No. 13/405,200, filed on Feb. 24, 2012.

(51) Int. Cl.
*G09B 23/30* (2006.01)
*A61K 35/12* (2015.01)
(Continued)

(52) U.S. Cl.
CPC ............. *G09B 23/303* (2013.01); *A61K 33/06* (2013.01); *A61K 33/14* (2013.01); *A61K 35/12* (2013.01); *A61K 35/14* (2013.01); *G09B 23/30* (2013.01)

(58) Field of Classification Search
USPC .......................................... 434/268
See application file for complete search history.

(56) References Cited

U.S. PATENT DOCUMENTS 3,549,747 A  12/1970 Krezanoski et al.
5,055,259 A  10/1991 Inoue et al.
(Continued)

FOREIGN PATENT DOCUMENTS

JP   2002-014105      1/2002
WO   WO 2011/084326 A2  7/2011
WO   WO 2013/126707 A1  8/2013

OTHER PUBLICATIONS

International Search Report for PCT/US2013/027329, mailed Jun. 13, 2013.
(Continued)

*Primary Examiner* — James Hull
(74) *Attorney, Agent, or Firm* — Nixon & Vanderhye P.C.

(57) ABSTRACT

Medical training kits and methods include a simulated liquid blood which simulates mammalian whole blood and a simulated hemostatic component. The simulated liquid blood includes a gellable component, and a simulated hemostatic component includes a gelling agent. The gelling agent causes the gellable component in the simulated liquid blood to form a mass of semi-solid or solid material in response the simulated blood being brought into contact therewith to thereby simulate blood clotting. In certain embodiments, the gellable component is chitosan and/or an alginate compound and the gelling agent is at least one compound which causes the gellable component to desolubulize, polymerize, complex, precipitate, cross-link and the like so as to form a (Continued)

semi-solid or solid mass of chitosan in response to physical contact between the simulated blood and the simulated hemostatic agent.

45 Claims, 6 Drawing Sheets

(51) Int. Cl.
    *A61K 33/14*     (2006.01)
    *A61K 35/14*     (2015.01)
    *A61K 33/06*     (2006.01)

(56) References Cited

U.S. PATENT DOCUMENTS

| | | | |
|---|---|---|---|
| 6,780,016 | B1 | 8/2004 | Toly |
| 7,534,107 | B2 | 5/2009 | Bardsley et al. |
| 7,968,114 | B2 | 6/2011 | Huey et al. |
| 8,367,388 | B2 | 2/2013 | Bloom et al. |
| 8,557,278 | B2 | 10/2013 | Huey et al. |
| 8,668,899 | B2 * | 3/2014 | Dowling ............. A61L 24/0026 424/1.13 |
| 2001/0033826 | A1 | 10/2001 | Roulier et al. |
| 2005/0181027 | A1 | 8/2005 | Messinger |
| 2005/0240137 | A1 | 10/2005 | Zhu et al. |
| 2007/0021703 | A1 | 1/2007 | McCarthy |
| 2007/0062865 | A1 | 3/2007 | Wang et al. |
| 2008/0031934 | A1 * | 2/2008 | MacPhee .......... A61F 13/00012 424/449 |
| 2008/0199539 | A1 | 8/2008 | Baker et al. |
| 2008/0299226 | A1 | 12/2008 | Mentkow et al. |
| 2008/0319476 | A1 | 12/2008 | Ward et al. |
| 2009/0175946 | A1 | 7/2009 | Gaissmaier et al. |
| 2011/0008760 | A1 | 1/2011 | Bevan et al. |
| 2011/0311632 | A1 | 12/2011 | Roorda et al. |
| 2012/0045742 | A1 | 2/2012 | Meglan et al. |
| 2013/0224712 | A1 | 8/2013 | Day et al. |

OTHER PUBLICATIONS

Runyon et al; "Minimal Functional Model of Hemostasis in a Biomimetic Microfluidic System", XP0025395621, Angew. Chem. Int. Ed., 2004, 43,1531-1536.
Snow et al; "The Navy Medical Technology Watch: Hemostatic Dressing Products for the Battlefield", XP055216006, Naval Health Research Center, Technical Document No. 07-1A, Sep. 9, 2006.
EP Appln. No. 13751913.8, Communication, Extended European Search Report, Oct. 9, 2015.
Written Opinion of the International Searching Authority for PCT/US2013/027329 mailed Jun. 13, 2013.
Sim Factor® Mock Blood and Clotting Kit, http://web.archive.org/web/*/https://www.simulution.com/shop-online/training-manikins/moulage-accessories/simfactor%C2%AE-mock-blood-and-clotting-agent-kit#producttabs-1 (Oct. 6, 2011) (3 pages).
Manual for SimFactor® Mock Blood and Clotting Kit, https://www.simulution.com/sites/delault/files/Simfactor%20Manual%20Rev.%201.pdf (Oct. 6, 2011) (1 page).

* cited by examiner

| Blood simulant | As-stained | As-washed | Observations |
|---|---|---|---|
| B3-1 | | | no obvious staining observed |
| B4-2 | | | no obvious staining observed |
| B4-7 | | | no obvious staining observed |
| B5-3 | | | very light staining observed in lighter colored regions of ACU material |
| B5-4 | | | very light staining observed in lighter colored regions of ACU material |
| B6-4 | | | No obvious staining |
| B6-6 | | | No obvious staining |

| Blood simulant | As-stained | Staining observations | As-washed | observations |
|---|---|---|---|---|
| Human whole blood |  | The blood did not immediately soak into the fabric, took 5-10 seconds before the blood absorbed into the fabric. The stain spread to a diameter of ~10cm | 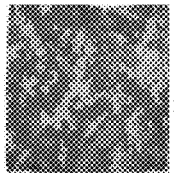 | Stain removed entirely |
| B3-1 | 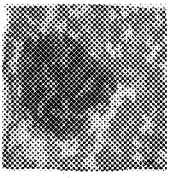 | initially pooled up for 3-5 seconds and absorbed into fabric after ~20 seconds. Color is light red, not nearly as vibrant as real blood. Stain spread to a diameter of ~10.5cm |  | Brown stain; clearly defined area of staining |
| B4-2 |  | slight pooling at first, absorbed into fabric after 3-5 seconds. Color is light red, not nearly as vibrant at real blood. Stain spread to a diameter of 11cm | 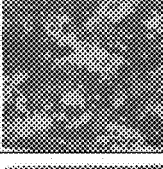 | Very light brown staining, perceivable in light colored areas of fabric |
| B4-7 | 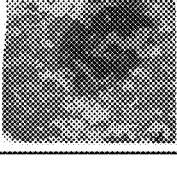 | quickly absorbed into fabric after ~5 seconds, very little pooling. Color is light red/brown, not nearly as vibrant as real blood. Stain spread to a diameter of 13cm | 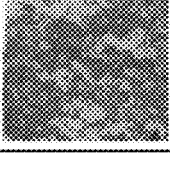 | Little to no staining; very light staining in colored areas of fabric |

FIG. 2A

| | | | | |
|---|---|---|---|---|
| B5-3 | 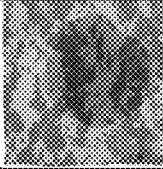 | slight pooling at first, absorbed into fabric after 3-5 seconds. Color is light red, not nearly as vibrant at real blood. Stain spread to a diameter of 12cm. | 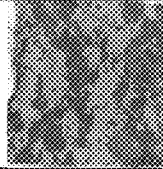 | Obvious light brown/pink |
| B5-4 |  | slight pooling at first, absorbed into fabric after 3-5 seconds. Color is darker red than other BS-865 formulations but not nearly as vibrant at real blood. Stain spread to a diameter of 12cm. |  | Obvious pink staining |
| B6-3 | 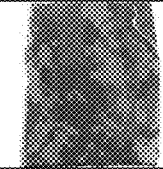 | | 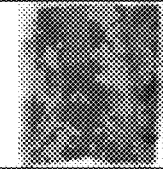 | No obvious staining |
| B6-5 | 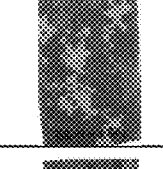 | | 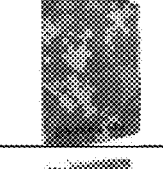 | No obvious staining |
| B6-6 | 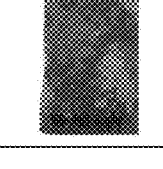 | | 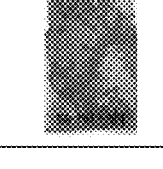 | Several obvious stains remained. Patches of red stain remained on the edges of the ACU fabric. |

FIG. 2B

| Dressing | Blood simulant | Pressure | Drainage time | Observations | Image |
|---|---|---|---|---|---|
| untreated gauze | B3-7 (50 mL) | 2 psi | 15 sec | small, diffuse, less viscous stain | |
| D5-1 | B3-7 (50 mL) | 2 psi | 13 sec | a small, concentrated, viscous gel | |
| untreated gauze | B3-7 (50 mL) | gravity | 27 sec | small, diffuse, non-adherent stain | |
| D5-1 | B3-7 (50 mL) | gravity | 84 sec | concentrated viscous gel | |
| D5-1 (2 ply) | B3-1 (35 mL) | 2 psi | 46 sec | very small piece of dark red gel on the dressing | |

FIG. 5A

| Dressing | Blood simulant | Pressure | Drainage time | Observations | Image |
|---|---|---|---|---|---|
| D5-1 (2 ply) | B5-6 (35 mL) | 2 psi | 11 sec | very thin gel layer on dressing surface | 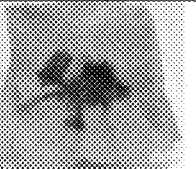 |
| D5-1 (2 ply) | B5-3 (35 mL) | 2 psi | >300 sec | large, gelatinous drip on the outer surface of the gauze and large gel in dressing |  |
| D5-1 (2 ply) | B5-7 (35 mL) | 2 psi | >300 sec | large, gelatinous drip on the outer surface and large gel in dressing | 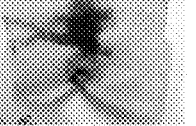 |
| D5-1 (2 ply) | B5-4 (25 mL) | 2 psi | 70 sec | Very large gels in the catch beaker; gel "clots" on the outer surface; medium sized gel "clot" on the inside surface | 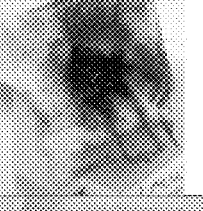 |
| D5-1 (2 ply) | B5-8 (25 mL) | 2 psi | >300 sec | Small gels formed in the catch beaker; medium sized, more localized gel "clot" on the inside surface |  |

FIG. 5B

MEDICAL TRAINING KITS AND METHODS TO SIMULATE TREATMENT OF UNCONTROLLED HEMORRHAGE

GOVERNMENT RIGHTS

This invention was made with Government support under Contract No. W81XWH-11-C-0062 awarded by the U.S. Army Medical Research Acquisition Activity (USAMRAA). The Government has certain rights to the invention.

CROSS-REFERENCE TO RELATED APPLICATION

This application is based on and claims priority from copending U.S. patent application Ser. No. 13/405,200 filed on Feb. 24, 2012, the entire content of which is expressly incorporated hereinto by reference.

FIELD

The embodiments disclosed herein relate generally to medical training kits and methods. In especially preferred forms, the embodiments disclosed herein relate to kits and methods to assist in the simulated trauma training of personnel (e.g., medical first responders) for treatment of hemorrhaging wounds.

BACKGROUND

Military first responders must be prepared to treat uncontrolled hemorrhage, which remains the primary cause of death from combat wounds. Simulated trauma training is the bridge that spans the gap between classroom study and live animal training and, ultimately, battlefield experience. It is critical, therefore, that simulated trauma training be as realistic and as up to date as possible in terms of wounding patterns and advanced technologies designed to treat such wounds in the field.

Unfortunately, current blood simulation technologies are limited to dyed water or other similarly unrealistic approximations that do not closely mimic the look, feel and biological properties of human blood. There is no known commercial product available that accurately replicates the coagulation and clotting properties of human blood, especially as it relates to training first responders in the use of current and developmental hemostatic products, such as QUICK CLOT® COMBAT GAUZE™ commercially available from Combat Medical Systems™ of Fayetteville, N.C., CHITOGAUZE™ commercially available from HemCon Medical Technologies, Inc. of Portland, Oreg., and CELOX™ gauze commercially available from Medtrade Products LTD. of Crewe, UK.

It is therefore towards fulfilling the need of more realistic personnel training for traumatic hemorrhage control that the embodiments as disclosed herein are directed.

SUMMARY

Medical training kits and methods are provided which include a simulated liquid blood which simulates mammalian whole blood and a simulated hemostatic component. The simulated liquid blood includes a gellable component. The simulated hemostatic component includes a gelling agent. The gelling agent causes the gellable component in the simulated liquid blood to form a mass of semi-solid or solid material in response to the simulated blood being brought into contact therewith to thereby simulate blood clotting.

According to some embodiments, the simulated liquid blood is a dilute acidic aqueous solution comprising chitosan as the gellable component. The chitosan may be present in the simulated blood formulation in an amount between about 0.6 to about 2.0 wt. %, and have a molecular weight of between about 50,000 Da to about 500,000 Da. In certain forms, the chitosan liquid can be autoclaved at temperatures between about 100 to about 150° C., at pressures of between about 5 to about 25 psi and a time of between about 1 minute to about 90 minutes and/or deacetylated so as to possess a percent deacetylation value (% DA) of at least about 70% (e.g., between about 70% to 100%).

Other embodiments of the simulated liquid blood may comprise an alginate compound dissolved in water. The alginate compound may be present in the simulated blood formulation in an amount between 0.05% and 2.0 wt. % and have a molecular weight of 10,000 Da to about 600,000 Da.

According to some embodiments, a dried simulated blood precursor version may also be made using granulated or powdered stocks of a chitosan or alginate compound. A liquid solvent may thus be added to such dried simulated blood precursors to bring the solution to a working volume of gellable liquid simulated blood. In the case of a dried chitosan formulation, granulated or powdered chitosan will be mixed with granulated or powdered acid (acetic or lactic acid, for example) and brought to a preferred working concentration of chitosan with the addition of water. In the case of a dried alginate formulation, granulated or powdered sodium alginate, for example, may be mixed with water and brought to a working concentration of alginate thus forming a gellable liquid simulated blood.

Additionally, some embodiments may also employ a concentrated form of chitosan or alginate gel or paste. A liquid solvent may thus be added to these concentrated components so as to bring the solution to a working volume of gellable liquid simulated blood. In the case of a concentrated chitosan formulation, a viscous chitosan concentrate will be mixed with water and brought to a preferred working concentration of chitosan thus forming a gellable liquid simulated blood. In the case of a concentrated alginate formulation, a viscous alginate concentrate will be mixed with water and brought to a working concentration of alginate thus forming a gellable liquid simulated blood.

The simulated blood closely approximates the look, feel, odor and biological properties of whole mammalian, especially human, blood. In this regard, the simulated blood formulation may comprise at least one colorant in an amount sufficient to mimic coloration of whole mammalian blood and/or at least one additive selected from the group consisting of viscosity modifiers (e.g., cellulosic materials), tactile agents (e.g., glycerol), scent modifiers and dispersants or surfactants.

In certain embodiments the medical training kits and methods will include a simulated blood which comprises chitosan as a gellable component, and a simulated hemostatic component which comprises a gelling agent in sufficient amount to cause the chitosan to gel (desolubilize, polymerize, precipitate, complex and/or cross-link) so as to form a semi-solid or solid mass of chitosan in response to physical contact between the simulated blood and the gelling agent. The gelling agent may be at least one selected from the group consisting of, for example, sodium tripolyphosphate (NaTPP), β-glycerophospate, sodium bicarbonate, sodium carbonate and Rose Bengal.

In other embodiments in which the simulated blood comprises an alginate compound as a gellable component, the gelling agent will preferably be selected from calcium salts, preferably calcium chloride.

The simulated hemostatic component may be in the form of a particulate (e.g., powder, granules or flakes) or liquid that may be brought into direct contact with the simulated blood. According to some embodiments, the simulated hemostatic component may include a carrier in or on which the gelling agent is provided. Suitable carriers for the gelling agent include liquids, gels and various physical substrates in the form of fabrics, gauzes, bandages, pads, sponges, dressings and the like typically encountered in the medical field. One embodiment of the hemostatic component may thus be in the form of a simulated hemostatic dressing which includes a fabric substrate carrying a particulate gelling agent.

In use, personnel (e.g., medical first responders) may be trained to treat wound hemorrhage by providing a simulated wound (e.g., a simulated wound associated with a training mannequin) and causing the simulated gellable liquid blood to flow into the wound in a manner that simulates hemorrhage. A simulated hemostatic component may thus be applied according to suitable treatment protocol to the wound in contact with the simulated blood. In such a manner, the gelling agent of the simulated hemostatic component is caused to interact physically with the gellable component of the simulated liquid blood and form a mass of semi-solid or solid material thereby simulating blood clotting.

These and other aspects of the present invention will become more clear after careful consideration is given to the following detailed description of a presently preferred exemplary embodiment thereof.

DEFINITIONS

As used herein and in the accompanying claims, the terms below are intended to have the following definitions.

"Simulated blood" means a flowable liquid medium which visually and tactilely simulates whole mammalian blood, especially whole human blood. A "simulated blood" will thus closely mimic the look and feel of whole blood in terms of coloration, viscosity, feel (e.g., stickiness), odor and/or clotting/caking characteristics in the presence of a simulated hemostatic agent.

"Gellable" means the ability of a liquid medium to form a mass or lump of solid or semi-solid (gel) material which in sufficient quantity impedes (or stops entirely) the ability of the liquid medium to flow.

"Gellation" means that the gellable material forms a mass or lump of solid or semi-solid material which is the result of insolubilization, precipitation, polymerization, crosslinking, complexation and the like.

A "gelling agent" is a substance which causes gel to form in a gellable liquid in response to physical contact between the liquid and the gelling agent. In a simulated blood, the gelling agent will thus be capable of desolubulizing, precipitating, polymerizing, complexing, cross-linking and the like a non-biological gellable component in the simulated blood so as to form a semi-solid or solid mass (clot) of the gellable component.

A "simulated hemostatic component" is a material that either stands alone in the form of a particulate (e.g., powder, granules or flakes) or is incorporated into or onto a liquid, gel or solid carrier and which includes at least one gelling agent.

"Simulated hemostatic dressing" means a fabric (usually a gauze) that has been treated with and thus carries a sufficient amount of at least one gelling agent.

"Chitosan liquid" means a solution or suspension of chitosan in a dilute acidic aqueous medium.

"Alginate liquid" means an aqueous solution or suspension of an alginate compound, typically sodium alginate.

"Fabric" means a collection of filaments, fibers and/or yarns which form a textile article having structural integrity. A fabric may thus be formed by means of conventional weaving, braiding, knitting, warp-knit weft insertion, spin-bonding, melt blowing techniques to form structurally integrated masses of filaments, fibers and/or yarns.

"Synthetic" means that a textile article is man-made from a fiber-forming substance including polymers synthesized from chemical compounds, modified or transformed natural polymers, and minerals. Synthetic fibers are thus distinguishable from natural fibers such as cotton, wool, silk and flax.

"Filament" means a fibrous strand of extreme or indefinite length.

"Fiber" means a fibrous strand of definite length, such as a staple fiber.

"Yarn" means a collection of numerous filaments or fibers which may or may not be textured, spun, twisted or laid together.

BRIEF DESCRIPTION OF FIGURES

Reference will be made herein to the accompanying FIGURES wherein:

FIGS. 2A and 2B are the interaction observation and stain removal testing results conducted according to Example 7;

FIGS. 5A and 5B are the flow testing results conducted according to Example 14.

DETAILED DESCRIPTION

Figure 1:
FIG. 1 provides the fabric stain testing results conducted according to Example 7.

Embodiments of the kits and methods as disclosed herein may include a simulated blood and a simulated hemostatic component which includes a gelling agent. According to certain embodiments, the simulated hemostatic component may be in the form of a simulated hemostatic dressing which includes a fabric substrate and a gelling agent carried by the fabric substrate. In other embodiments, the simulated hemostatic component is in the form of a simulated hemostatic agent, which comprises at least one gelling agent in the form of a particulate (e.g., powder, granule or flake). In use, the simulated blood may thus be provided as a source of blood flowing from a simulated wound (e.g., as may be provided in a task training kit, a training mannequin or the like). The simulated hemostatic component (e.g., the gelling agent serving as a simulated hemostatic powder or a simulated hemostatic dressing comprised of a fabric and a gelling agent carried by the fabric) may thus be used by personnel being trained (e.g., a medical first responder trainee) in a simulated treatment of a hemorrhaging wound.

A. Simulated Blood Component

The simulated blood component is a flowable liquid which visually and tactilely mimics natural whole mammalian (preferably human) blood. In certain preferred embodiments, the simulated blood is a flowable liquid having a viscosity at room temperature (20° C.) of between about 1 to about 6 cP, more preferably between about 3 to about 5 cP. Viscosities of the simulated blood at room temperature up to about 100 cP may however be employed. The simulated blood in especially preferred embodiments includes chitosan which is dissolved or suspended in an acidic aqueous liquid or an alginate compound (e.g., sodium alginate) dissolved or suspended in water, and a colorant sufficient to achieve a red color simulating whole blood.

Virtually any form of chitosan that is soluble in an acidic aqueous liquid may be employed in the embodiments disclosed herein. Thus, a wide variety of commercially available forms of chitosan having a range of molecular weights of between about 50,000 Da to about 500,000 Da may be employed. In this regard, the molecular weight, concentration and degree of deacetylation of the chitosan can be selected so as to achieve the desired combination of properties (e.g., viscosity, appearance, gellability and the like) to mimic whole blood.

Virtually any form of an alginate compound that is soluble in water, such as sodium alginate, may be employed in the embodiments disclosed herein. Thus a wide variety of commercially available forms of alginate having a range of molecular weights of between 10,000 Da to 600,000 Da may be employed. In this regard, the molecular weight and concentration of alginate compound can be selected so as to achieve the desired combination of properties (e.g., viscosity, appearance, gellability and the like) to mimic whole blood.

The molecular weight of the chitosan, and hence the viscosity of the chitosan liquid, can be adjusted by conventional autoclaving technique. Specifically, the viscosity of the chitosan liquid may be decreased by autoclaving a chitosan liquid containing a relatively higher molecular weight chitosan for a suitable time period to achieve the desired viscosity properties of the chitosan liquid. Autoclaving may also impart a brownish coloration and opacity to the chitosan liquid which, when combined with a subsequently added colorant, more closely mimics the reddish-brown coloration and opacity of whole blood. Suitable autoclaving conditions include autoclave temperatures of between about 100 to about 150° C., autoclave pressures of between about 5 to about 25 psi and a time of between about 1 minute to about 90 minutes, more preferably about 120-125° C. at 10-15 psi for about 10 to about 90 minutes. Suitable autoclaving conditions include a temperature of about 121° C., a pressure of about 15 psi and a time of about 15 or 75 minutes.

The viscosity of an alginate-based liquid can be adjusted by simple dilution with water or by adding increased amounts of the alginate compound.

The chitosan employed in the simulated blood component preferably has a percent deacetylation value (% DA) of at least about 70%, more preferably between about 80% to 100%. In certain embodiments, the chitosan will have a % DA of between about 85% to about 95%. Deacetylation can be achieved by subjecting chitosan to deacetylation conditions, for example, contacting the chitosan at elevated temperature (e.g., about 120° C.) with a basic solution (e.g., sodium hydroxide), under nitrogen for a sufficient time period (e.g., between about 1 to about 3 hours).

The chitosan-based simulated blood component will typically comprise between about 0.6 to about 2.0 wt. %, more preferably between about 1.0 to about 1.5 wt. %, of chitosan. As noted above, the chitosan is preferably dissolved or suspended in a dilute acidic aqueous liquid having a pH of between about 4 to about 6, more preferably between about 4 to about 5. Virtually any dilute acid may be employed, for example, acetic acid, lactic acid, dilute hydrochloric (HCl) acid and the like. One preferred acidic liquid includes an aqueous acetic acid solution having an acetic acid concentration of between about 0.03 M to about 0.10 M, preferably between about 0.075 M to about 0.1 M.

The alginate-based simulated blood component will typically comprise between about 0.05% to about 2.0 wt. %, more preferably between about 0.2 to about 0.5 wt. %, of the alginate compound. As noted above, the alginate compound is preferably dissolved or suspended in water (preferably deionized water) having a pH of between 6 to about 8, more preferably between about 6.5 to about 7.

Virtually any colorant that does not cause polymerization, cross-linking, complexation and/or precipitation of the chitosan or alginate compound can be employed to achieve the coloration of the simulated blood component that is desired to mimic the coloration of whole blood. The colorant may thus be one or more organic and/or inorganic liquid or pigment color additive that is capable of being dissolved or suspended in the acidic chitosan liquid or water-borne alginate solution.

Suitable colorants include, for example, Red 40 dye, Red 40 Lake, alizarin (1,2-dihydroxyanthraquinone) crimson pigment, lac dye pigment, oenin chloride (malvidin-3-O-glucoside chloride), quinacridone red pigment (5,12-dihydro-quino[2,3-b]acridine-7,14-dione), venetian red pigment, napthol red pigment and concentrated (e.g., 2× to 4×) natural cherry juice (or other red fruit extracts). The colorant may be used alone or as combinations of two or more of the same. Most preferably, the colorant is provided in the simulated blood component to achieve red-green-blue (RGB) color coordinates of comparable to whole blood, i.e., a red (R) coordinate of about 94±9, a green (G) coordinate of about 37±3 and a blue (B) coordinate of about 40±4. The R-coordinate may thus range from about 45 to about 110, the G-coordinate may range from about 25 to about 55 and the B-coordinate may range from about 30 to about 50.

A variety of optional additives may be employed to provide the desired physical properties to either the simulated blood or to the simulated "clot" that result from interaction of the simulated blood with the simulated hemostatic agent. For example, a viscosity modifier (e.g., a cellulosic such as methyl cellulose) may be added to the simulated blood component to impart desirable viscosity characteristics (e.g., so as to provide greater "tackiness"). Suitable tactile agents, such as glycerol, may be employed to impart suitable "stickiness" to the simulated blood component. Glycerol also has an added benefit of decreasing clothing fabric staining tendencies of the simulated blood component.

Scented agents may be added to lend a realistic blood/biological odor to the simulated blood. Such compounds of, for example, 1-octen-3-one or small amounts of metallic or iron based additives may be employed to lend a "metallic" smell to the solution. Certain antimicrobial/anti-spoilage compounds may be added to prolong shelf-life of the solutions and prevent contamination due to bacteria, mold or fungus. Suitable additives such as sodium benzoate, polysorbates or other anti-microbial/spoilage compounds may be employed. Dispersant compounds may be added to aid in colorant dispersal and to prevent clumping of colorant additives. Nonionic dispersants such as TRITON™ X surfactants (i.e., nonionic surfactants having a hydrophilic polyethylene oxide chain and an aromatic hydrocarbon lipophilic or hydrophobic group (e.g., a 4-phenyl group) are preferred but other suitable dispersing agents may be added. Additionally, stain removal additives may also be employed to aid in removing colorant compounds from clothing or equipment. Glycerol when present as an additive may aid in this regard but other stain removal additives may also be incorporated into the formulation.

The optional additives may be employed in amounts between 0 to about 40 wt. % of the simulated blood component. For example, a viscosity modifier may be employed in an amount of up to about 5.0 wt. %, and if employed may be present in an amount of between about 1.0 wt. % to about 5.0 wt. %, preferably between about 1.5 wt. % to about 3.5 wt. %. A tactile agent may additionally (or alternatively) be employed in an amount of up to about 30 wt. %, and if employed may be present in an amount between about 1.0 wt. % to about 30 wt. %, preferably between about 5 wt. % to about 25 wt. %.

The preferred scent additive is 1-octen-3-one which may be employed in an amount up to 1 mM, and if employed may be present in an amount between 1 nM and 1 mM, preferably between 100 nM to 200 nM.

The preferred antimicrobial/antispoilage additive is sodium benzoate which may be employed in an amount up to 1 wt. %, and if employed may be present in an amount between 0.01 wt % and 1 wt. %, preferably between 0.05 wt % and 0.2 wt %.

One preferred embodiment of a chitosan-based blood simulant will comprise 1.5 wt. % low molecular weight chitosan, 16.9 mg/mL Red 40 Lake, 9.9 µg/mL Blue 1 Lake, 0.1% Triton™ X-100 and 0.1% sodium benzoate in 0.1 M lactic acid. If blood-like scent is desired, 1-octen-3-one would be added to a concentration of 150 nM.

A simulated chitosan-based blood component may be prepared by dissolving or suspending powdered chitosan of an appropriate degree of deacetylation in a dilute acidic aqueous liquid heated to a temperature between about 65° C. to about 80° C. to form a base chitosan liquid. Undissolved chitosan may be allowed to settle from the base liquid for removal by any suitable separation technique (e.g., vacuum filtration through 5 µm filtration membrane). In some embodiments, the base chitosan liquid may then be autoclaved under the conditions noted previously so as to reduce viscosity or impart opacity and/or a brownish coloration to the base chitosan solution. The colorant and other optional additives may then be blended into the base chitosan liquid. The resulting liquid may then be allowed to stand so as to settle out non-dissolved/suspended material and subjected to separation (e.g., vacuum filtration). The chitosan-based simulated blood component that is obtained may be collected and stored in a suitable container until use.

An alginate-based simulated blood component may also be prepared by dissolving or suspending a powdered alginate compound of an appropriate molecular weight in water. Heating and/or stirring may be employed to dissolve the alginate in the water. The resulting liquid may be filtered to remove non-dissolved/suspended material and subjected to separation (e.g., vacuum filtration). The alginate-based simulated blood component that is obtained may be collected and stored in a suitable container until use.

B. Simulated Hemostatic Component

Embodiments of the simulated hemostatic component will necessarily include a gelling agent for gelling the gellable component in the simulated blood so as to mimic blood "clotting" when brought into physical contact with the simulated blood. In certain embodiments the simulated hemostatic component will be in the form of a simulated hemostatic dressing which includes a fabric substrate which carries the gelling agent. In other embodiments, the simulated hemostatic component will be in the form of a hemostatic particulate, liquid or gel material containing the gelling agent which can be brought directly into contact with the simulated blood.

The gelling agent is any material which on contact with the simulated blood component causes the gellable component in the simulated blood to desolubulize, polymerize, complex, precipitate and/or cross-link so as to form a semi-solid or solid mass. It is the formation of the mass of semi-solid or solid gellable component which thus simulates blood clotting in response to the physical contact between the simulated hemostatic component and the simulated blood.

Preferred gelling agents for use in the simulated hemostatic dressing component include, for example, sodium tripolyphosphate (NaTPP), calcium salts (e.g., calcium chloride), β-glycerophospate, sodium bicarbonate, sodium carbonate, sodium citrate, citric acid and Rose Bengal. Sodium tripolyphosphate is the preferred gelling agent when chitosan is the gellable component. Calcium chloride is the preferred gelling agent when an alginate compound (e.g., sodium alginate) is the gellable component. When the simulated hemostatic component is in the form of a simulated hemostatic dressing comprising a fabric substrate carrying the gelling agent, the gelling agent will preferably be present on and/or in the fabric substrate in an amount of between about 10 wt. % to about 80 wt. %, for example between about 50 wt. % to about 70 wt. %, based on the weight of the fabric substrate.

The fabric substrate employed in a simulated hemostatic dressing embodiment may be formed of virtually any synthetic and/or natural fiber and/or filament material and may be in the form of a woven or non-woven textile structure. In preferred embodiments, the fabric substrate is a relatively loosely woven gauze formed of filaments or yarns comparable to commercially available hemostatic dressing products. Suitable filaments and/or yarns that may be employed to form the fabric substrate include, but are not limited to, polyester, nylon, rayon and cotton. Blends of such filaments and yarns may also be employed if desired.

A binder may optionally be employed to suitably bind the simulated hemostatic agent to the fabric substrate. Suitable binders include, for example, agarose, powdered gelatin (Type A and/or Type B), sodium alginate, carboxymethylcellulose and methyl cellulose. One or more than one binder may be mixed with the simulated hemostatic agent and applied onto the fabric substrate. Alternatively the binder may be applied onto the fabric substrate prior or subsequent to the application of the simulated hemostatic agent. For example, according to one embodiment, sodium tripolyphosphate may be applied onto the fabric substrate, followed by the application of a gelatin binder to the substrate.

The gelling agent and, if employed, the binder may be applied to the fabric substrate in any suitable manner. For example, the gelling agent and optional binder may be dissolved in a suitable solvent (preferably water) and applied to the fabric substrate by dipping, padding, spraying, roll-coating or like techniques. By way of example, when NaTPP is employed as a gelling agent, it may be applied onto the fabric substrate as a 20 wt. % solution of NaTPP by either spraying the solution onto the fabric substrate or submersing the fabric substrate into the solution. Subsequent drying of the thus NaTPP-treated fabric substrate will leave a dried solid residue of the NaTPP which is then capable of gelling the simulated blood component when brought into contact therewith.

EXAMPLES

The present invention will be further understood by reference to the following non-limiting Examples.

Example 1A

Chitosan-Based Simulated Blood Formulations

Different simulated blood formulations as identified in Table 1 below were prepared by combining (1) a base chitosan liquid, (2) colorant(s) and optionally (3) other additives. In each example, commercially available grades of chitosan having a percent deacetylation value (% DA) of between about 70% to about 80% and having molecular weight between about 50,000 Da and 500,000 Da were employed. Some chitosan variants were further deacetylated by stirring the chitosan in 120° C. 50% aqueous sodium hydroxide under nitrogen for 2.5 hours. The further deacetylated chitosan was thereafter filtered and recovered as a powder before preparing the base chitosan liquid. A chitosan liquid was formed by adding a chitosan variant to an acidic aqueous medium (i.e., acetic acid). In certain instances, the chitosan liquid was autoclaved under autoclaving conditions of 121° C., 15 psi for either 15 minutes or 75 minutes. The following summarizes the base chitosan liquids that were used in the simulated blood formulations of this Example 1:

LMW=Commercial low molecular weight chitosan with no further deacetylation and no autoclaving of the chitosan liquid aLMW=Commercial low molecular weight chitosan with no further deacetylation but autoclaving of the chitosan liquid for 15 minutes aDALMW=Commercial low molecular weight chitosan with further deacetylation and autoclaving of the chitosan liquid for 15 minutes a75LMW=Commercial low molecular weight chitosan with no further deacetylation but autoclaving of the chitosan liquid for 75 minutes DAMMW=Commercial medium molecular weight chitosan further deacetylated and no autoclaving of the chitosan liquid a75DAMMW=Commercial medium molecular weight chitosan further deacetylated with autoclaving of the chitosan liquid for 75 minutes Example 1B Alginate-Based Simulated Blood Formulations Different simulated blood formulations as identified in Table 1 below were prepared by combining (1) a base alginate liquid, (2) colorant(s) and optionally (3) other additives. In each example, commercially available grades of sodium alginate having molecular weight between about 10,000 Da and 600,000 Da were employed. An alginate liquid was formed by dissolving or suspending an alginate variant in water.

TABLE 1

Blood Simulant Formulations

| # | Gellable Component | | | Colorant |
|---|---|---|---|---|
|  | type | Conc. (%) | solvent | Type and concentration |
| B1-1 | LWM | 2% | 0.1M AA | — |
| B1-2 | LMW | 1% | 0.05M AA | 6.25 mg/mL Alizarin crimson pigment |
| B1-3 | aLMW | 1% | 0.05M AA | 6.12 mg/mL Aluminum Lake FD&C red #40 |
| B2-1 | aLWM | 1.5 | 0.075M AA | 5.00 mg/mL Alizarin crimson pigment |
| B2-2 | aLWM | 1.5 | 0.075M AA | 5.00 mg/mL Jacquard red acid dye |
| B2-3 | aLWM | 1.5 | 0.075M AA | 5.00 mg/mL Jacquard Procion MX red reactive cold water dye |
| B2-4 | aLMW | 1.5 | 0.075M AA | 25% Concentrated natural cherry juice |
| B3-1 | LWM | 1.5 | 0.075M AA | 25% 4× concentrated natural cherry juice |
| B3-2 | LWM | 1.5 | 0.075M AA | 6.25 mg/mL erythrosine B |
| B3-3 | LWM | 1.5 | 0.075M AA | 5.00 mg/mL Rose Bengal |
| B3-4 | LMW | 1.5 | 0.075M AA | 10.0 mg/mL carminic acid |
| B3-5 | aLMW | 1.5 | 0.075M AA | 25% 4× concentrated natural cherry juice |
| B3-6 | LMW | 1.5 | 0.1M AA | 25% 2× concentrated natural cherry juice |
| B3-7 | aLMW | 1.16 | 0.058M AA | 2.72 mg/mL Alizarin crimson pigment |
|  |  |  |  | 0.64 mg/mL Venetian red pigment |
|  |  |  |  | 1.28 mg/mL Lac dye pigment |
|  |  |  |  | 7.25% 4× concentrated natural cherry juice |
| B4-1 | aLWM | 1.6 | 0.078M AA | 3.9 mg/mL Alizarin crimson pigment |
|  |  |  |  | 2.4 mg/mL Venetian red pigment |
|  |  |  |  | 0.39 mg/mL Lac dye pigment |
|  |  |  |  | 1.57 mg/mL Pthalo blue pigment |
| B4-2 | aLWM | 1.0 | 0.050M AA | 5.0 mg/mL Alizarin crimson pigment |
|  |  |  |  | 1.0 mg/mL Venetian red pigment |
|  |  |  |  | 1.0 mg/mL Pthalo blue pigment |
| B4-3 | aLWM | 1.1 | 0.053M AA | 4.1 mg/mL Alizarin crimson pigment |
|  |  |  |  | 0.86 mg/mL Venetian red pigment |
|  |  |  |  | 0.51 mg/mL Lac dye pigment |
|  |  |  |  | 0.60 mg/mL Pthalo blue pigment |
|  |  |  |  | 2.9% 4× concentrated natural cherry juice |

TABLE 1-continued

Blood Simulant Formulations

| # | Gellable Component type | Conc. (%) | solvent | Colorant Type and concentration |
|---|---|---|---|---|
| B4-4 | aLMW | 0.60 | 0.030M AA | 3.0 mg/mL Alizarin crimson pigment<br>0.60 mg/mL Venetian red pigment<br>0.60 mg/mL Pthalo blue pigment<br>40% 4× concentrated natural cherry juice |
| B4-5 | aDA-LMW | 1.2 | 0.060M AA | 6.0 mg/mL Alizarin crimson pigment<br>1.2 mg/mL Venetian red pigment<br>40% 4× concentrated natural cherry juice |
| B4-6 | aLMW | 1.0 | 0.067M AA | 6.7 mg/mL Alizarin crimson pigment<br>33% 2× concentrated natural cherry juice |
| B4-7 | aDA-LMW | 1.0 | 0.067M AA | 6.7 mg/mL Alizarin crimson pigment<br>33% 2× concentrated natural cherry juice |
| B5-1 | a75LWM | 2.0 | 0.1M AA | 13 mg/mL Alizarin crimson pigment<br>2.8 mg/mL Venetian red pigment |
| B5-2 | a75LWM | 1.5 | 0.075M AA | 2.0 mg/mL Alizarin crimson pigment<br>1.4 mg/mL Venetian red pigment<br>25% 2× concentrated natural cherry juice |
| B5-3 | a75LMW | 1.5 | 0.075M AA | 2.0 mg/mL Alizarin crimson pigment<br>1.4 mg/mL Venetian red pigment<br>0.78 mg/mL Quinacridone red pigment<br>25% 2× concentrated natural cherry juice |
| B5-4 | a75LMW | 2.0 | 0.1M AA | 2.7 mg/mL Alizarin crimson pigment<br>1.8 mg/mL Venetian red pigment<br>1.0 mg/mL Quinacridone red pigment |
| B5-5 | aLMW | 1.0 | 0.05M AA | 5.0 mg/mL Alizarin crimson pigment<br>1.0 mg/mL Venetian red pigment<br>50% 4× concentrated natural cherry juice |
| B5-6 | DA-MMW | 1.5 | 0.075M AA | 25% 4× concentrated natural cherry juice |
| B5-7 | DA-MMW | 1.5 | 0.075M AA | 2.0 mg/mL Alizarin crimson pigment<br>1.4 mg/mL Venetian red pigment<br>0.78 mg/mL Quinacridone red pigment<br>25% 2× concentrated natural cherry juice |
| B5-8 | DA-MMW | 2.0 | 0.1M AA | 2.7 mg/mL Alizarin crimson pigment<br>1.8 mg/mL Venetian red pigment<br>1.0 mg/mL Quinacridone red pigment |
| B6-1 | a75LMW | 1.5 | 0.075M AA | 25% 2× concentrated natural cherry juice |
| B6-2 | a75DAMMW | 2.0 | 0.1M AA | 2.7 mg/mL Alizarin crimson pigment<br>1.8 mg/mL Venetian red pigment<br>1.0 mg/mL Quinacridone red pigment |
| B6-3 | aDALMW | 0.71 | 0.036M AA | 3.6 mg/mL Alizarin crimson pigment<br>0.71 mg/mL Venetian red pigment<br>36% 4× concentrated natural cherry juice<br>28% glycerol |
| B6-4 | a75LMW | 1.1 | 0.054M AA | 1.4 mg/mL Alizarin crimson pigment<br>0.89 mg/mL Venetian red pigment<br>0.56 mg/mL Quinacridone red pigment<br>18% 2× concentrated natural cherry juice<br>28% glycerol |
| B6-5 | aLMW | 1.1 | 0.054M AA | 18% 4× concentrated natural cherry juice<br>28% glycerol |
| B6-6 | a75LMW | 1.4 | 0.071M AA | 1.9 mg/mL Alizarin crimson pigment<br>1.2 mg/mL Venetian red pigment<br>0.71 mg/mL Quinacridone red pigment<br>28% glycerol |
| B6-7 | a75LMW | 2.0 | 0.1M AA | 2.7 mg/mL Alizarin crimson pigment<br>1.8 mg/mL Venetian red pigment<br>1.0 mg/mL quinacridone red pigment<br>1.6 mg/mL methyl cellulose |
| B6-8 | a75LMW | 2.0 | 0.1M AA | 2.7 mg/mL Alizarin crimson pigment<br>1.8 mg/mL Venetian red pigment<br>1.0 mg/mL Quinacridone red pigment<br>3.3 mg/mL methyl cellulose |
| B6-9 | a75LMW | 1.5 | 0.1M AA | 2.7 mg/mL Alizarin crimson pigment<br>1.8 mg/mL Venetian red pigment<br>1.0 mg/mL Quinacridone red pigment<br>12.5 µg/mL Oenin chloride |
| B2.1-1 | a75LMW | 2.0 | 0.1M AA | 1.7 mg/mL napthol red pigment<br>0.73 mg/mL Venetian red pigment |
| B2.1-2 | a75LMW | 2.0 | 0.1M AA | 2.8 mg/mL napthol red pigment |
| B2.1-3 | a75LMW | 2.0 | 0.1M AA | 1.8 mg/mL napthol red pigment<br>0.5 mg/mL alizarin crimson pigment |
| B2.2-1 | a75LMW | 2.0 | 0.1M AA | 1.7 mg/mL napthol red pigment<br>1.2 mg/mL alizarin crimson pigment |
| B2.2-2 | LMW | 2.0 | 0.1M AA | 1.7 mg/mL napthol red pigment<br>1.2 mg/mL alizarin crimson pigment |

TABLE 1-continued

Blood Simulant Formulations

| # | Gellable Component type | Conc. (%) | solvent | Colorant Type and concentration |
|---|---|---|---|---|
| B2.2-3 | LMW | 2.0 | 0.1M AA | 1.7 mg/mL napthol red pigment |
| | | | | 0.67 mg/mL Venetian red pigment |
| | | | | 0.67 mg/mL alizarin crimson pigment |
| B2.2-4 | LMW | 1.5 | 0.1M AA | 1.7 mg/mL napthol red pigment |
| | | | | 0.67 mg/mL Venetian red pigment |
| | | | | 0.67 mg/mL alizarin crimson pigment |
| B2.3-1 | LMW | 1.5 | 0.1M AA | 5 mg/mL Venetian red pigment |
| | | | | 1.7 mg/mL napthol red pigment |
| B2.3-2 | LMW | 1.5 | 0.1M AA | 3.3 mg/mL Venetian red pigment |
| | | | | 3.3 Alizarin crimson pigment |
| | | | | 1.7 mg/mL napthol red pigment |
| B2.3-3 | LMW | 1.5 | 0.1M AA | 5 mg/mL Alizarin crimson pigment |
| B2.3-4 | LMW | 1.5 | 0.1M AA | 3.3 mg/mL Lac dye pigment |
| | | | | 3.3 mg/mL Venetian red pigment |
| | | | | 1.7 mg/mL napthol red pigment |
| B2.3-5 | LMW | 1.5 | 0.1M AA | 3.3 mg/mL Lac dye pigment |
| | | | | 1.7 mg/mL napthol red pigment |
| | | | | 0.83 mg/mL Venetian red pigment |
| B2.3-6 | LMW | 1.5 | 0.1M AA | 5 mg/mL Alizarin crimson pigment |
| | | | | 0.83 mg/mL Venetian red pigment |
| B2.3-7 | LMW | 1.5 | 0.1M AA | 5 mg/mL Alizarin crimson pigment |
| | | | | 0.33 mg/mL napthol red pigment |
| B2.3-8 | LMW | 1.5 | 0.1M AA | 5 mg/mL Alizarin crimson pigment |
| | | | | 3.3 mg/mL Venetian red pigment |
| B2.4-1 | LMW | 1.5 | 0.1M AA | 4 mg/mL phthalo blue pigment |
| | | | | 1.7 mg/mL napthol red pigment |
| | | | | 1.3 mg/mL Venetian red pigment |
| B2.4-2 | LMW | 1.5 | 0.1M AA | 3.3 mg/mL naphthol red pigment |
| | | | | 3.3 mg/mL phthalo blue pigment |
| B2.4-3 | LMW | 1.5 | 0.1M AA | 3.3 mg/mL alizarin crimson pigment |
| | | | | 1.7 mg/mL napthol red pigment |
| B2.4-4 | LMW | 1.5 | 0.1M AA | 3.3 mg/mL alizarin crimson |
| | | | | 0.67 mg/mL napthol red pigment |
| B2.4-5 | LMW | 1.5 | 0.1M AA | 2.5 mg/mL Red Lake #40 dye |
| B2.4-6 | LMW | 1.0 | 0.1M AA | 5.0 mg/mL red lake #40 dye |
| B2.4-7 | LMW | 2.0 | 0.1M AA | 5.0 mg/mL red lake #40 dye |
| B2.4-8 | LMW | 1.5 | 0.1M LA | 2.5 mg/mL Red Lake #40 dye |
| B2.4-9 | LMW | 1.0 | 0.1M LA | 0.5 mg/mL red lake #40 dye |
| B2.4-10 | LMW | 2.0 | 0.1M LA | 1.7 mg/mL napthol red pigment |
| | | | | 0.67 mg/mL Venetian red pigment |
| | | | | 0.67 mg/mL alizarin crimson pigment |
| B2.4-11 | LMW | 2.0 | 0.1M LA | 1.7 mg/mL napthol red pigment |
| | | | | 0.67 mg/mL Venetian red pigment |
| | | | | 0.67 mg/mL alizarin crimson pigment |
| | | | | $1.3 \times 10^{-5}$ % oct-1-en-3-one |
| B2.4-12 | LMW | 1.5 | 0.1M LA | 1.7 mg/mL napthol red pigment |
| | | | | 0.67 mg/mL Venetian red pigment |
| | | | | 0.67 mg/mL alizarin crimson pigment |
| | | | | $6.7 \times 10^{-6}$ % oct-1-en-3-one |
| B2.4-13 | LMW | 1.5 | 0.075M LA | 2.5 mg/mL red dye 40 |
| B2.5-1 | LMW | 1.4 | 0.1M LA | 9% glycerol |
| | | | | 3.3 mg/mL Venetian red pigment |
| | | | | 2.5 mg/mL alizarin crimson pigment |
| | | | | 1.7 mg/mL napthol red |
| | | | | 0.45 mg/mL sodium benzoate |
| B2.5-2a | LMW | 1.4 | 0.95M LA | 4.5% glycerol |
| | | | | 0.83 mg/mL napthol red pigment |
| | | | | 1.7 mg/mL Venetian red pigment |
| | | | | 1.2 mg/mL alizarin crimson pigment |
| | | | | 0.45 mg/mL sodium benzoate |
| B2.5-2b | LMW | 1.4 | 0.95M LA | 4.5% glycerol |
| | | | | 0.83 mg/mL napthol red pigment |
| | | | | 1.7 mg/mL Venetian red pigment |
| | | | | 1.2 mg/mL alizarin crimson pigment |
| | | | | 0.45 mg/mL sodium benzoate |
| | | | | 120 nM 1-octen-3-one |
| B2.5-3 | LMW | 2 | 0.1M LA | 3.3 mg/mL Cadmium red (dark) pigment |
| | | | | 1.7 mg/mL Napthol red pigment |
| | | | | 0.05% sodium benzoate |
| B2.5-4 | LMW | 1.5 | 0 1M LA | 3.3 mg/mL Cadmium red (dark) pigment |
| | | | | 0.33 mg/ml Napthol red pigment |
| | | | | 0.05% sodium benzoate |

TABLE 1-continued

Blood Simulant Formulations

| # | Gellable Component | | | Colorant |
|---|---|---|---|---|
| | type | Conc. (%) | solvent | Type and concentration |
| B2.5-5 | LMW | 1.5 | 0.1M LA | 3.3 mg/mL Mars red extra deep pigment<br>0.33 mg/mL Chinese red vermillion pigment<br>0.05% sodium benzoate |
| B2.5-6 | LMW | 1.5 | 0.1M LA | 3.3 mg/mL Cadmium red (dark) pigment<br>0.5 mg/ml Chinese red vermillion pigment<br>0.05% sodium benzoate |
| B2.5-7 | LMW | 1.8 | 0.09M LA | 10% glycerol<br>2.2 mg/mL Cadmium red (dark) pigment<br>1.1 mg/ml Napthol red pigment<br>0.05% sodium benzoate |
| B2.5-8 | LMW | 1.9 | 0.09M LA | 5% glycerol<br>1.7 mg/mL Cadmium red (dark) pigment<br>0.84 mg/ml Napthol red pigment<br>0.05% sodium benzoate |
| B2.5-9 | LMW | 1.4 | 0.09M LA | 10% glycerol<br>1.5 mg/mL Cadmium red (dark) pigment<br>0.75 mg/ml Napthol red pigment<br>0.05% sodium benzoate |
| B2.5-10 | LMW | 1.4 | 0.09M LA | 5% glycerol<br>1.7 mg/mL Cadmium red (dark) pigment<br>0.84 mg/ml Napthol red pigment<br>0.05% sodium benzoate |
| B2.5-11 | LMW | 1.5 | 0.1M LA | 1% glycerol<br>1.6 mg/mL Carmine alum lake |
| B2.6-1 | LMW | 1.5 | 0.1M LA | 3.3 mg/mL Mars Red Extra Deep pigment<br>0.33 mg/mL Cadmium Red (medium) pigment<br>0.05% sodium benzoate |
| B2.6-2 | LMW | 1.5 | 0.1M LA | 10 mg/mL Alizarin Crimson pigment<br>2.0 mg/mL Venetian Red pigment<br>2 mg/mL Pthalo Blue pigmen<br>0.05% sodium benzoate |
| B2.6-3 | LMW | 1.5 | 0.1M LA | 3.3 mg/mL Cadmium Red (deep) pigment<br>3.3 mg/mL Cadmium Red (medium) pigment<br>0.05% sodium benzoate |
| B2.6-4 | LMW | 1.5 | 0.1M LA | 5.0 mg/mL Caput Mortuum pigment<br>0.33 mg/mL Cadmium red (medium) pigment<br>0.05% sodium benzoate |
| B2.6-5 | LMW | 1.5 | 0.1M LA | 3.3 mg/mL Madder Lake pigment<br>1.7 mg/mL Purple-Red pigment<br>0.05% sodium benzoate |
| B2.6-6 | LMW | 1.5 | 0.1M LA | 3.3 mg/mL Red 40 Lake dye<br>1 µL/mL Triton X-100<br>0.05% sodium benzoate |
| B2.6-7 | LMW | 1.5 | 0.1M LA | 1.7 mg/mL Purple-Red pigment<br>1.7 mg/mL Red 40 Lake dye<br>0.5 µL/mL Triton X-100<br>0.05% sodium benzoate |
| B2.6-8 | LMW | 1.5 | 0.1M LA | 2.5 mg/mL Red 40 Lake dye<br>0.83 mg/mL Purple-Red pigment<br>0.75 µL/mL Triton X-100<br>0.05% sodium benzoate |
| B2.6-9 | LMW | 1.5 | 0.1M LA | 1.5 mg/mL Purple-Red pigment<br>1.5 mg/mL Red 40 Lake dye<br>25 µL/mL glycerol<br>0.15 µL/mL Triton X-100<br>0.05% sodium benzoate |
| B2.6-10 | LMW | 1.5 | 0.1M LA | 24 µL/mL glycerol<br>0.097 mL/mL triton™ X-100<br>3.3 mg/mL Purple Red pigment<br>3.3 mg/mL Red 40 Lake dye<br>0.1% sodium benzoate |
| B2.6-11 | LMW | 1.5 | 0.1M LA | 24 µL/mL glycerol<br>0.97 µL/mL Triton ™ X-100<br>0.70 mg/mL Lac Dye powder (Rubley)<br>2.6 mg/mL Red 40 Lake powder<br>0.97 mg/mL iron oxide pigment<br>0.1% sodium benzoate |
| B2.6-12 | LMW | 1.5 | 0.1M LA | 2.6 mg/mL Red 40 Lake powder<br>0.70 mg/mL Lac dye powder (Rublev)<br>15 µL/mL glycerol<br>0.98 µL/mL Triton ™ X-100 |

TABLE 1-continued

Blood Simulant Formulations

| # | Gellable Component type | Conc. (%) | solvent | Colorant Type and concentration |
|---|---|---|---|---|
| B2.6-13 | LMW | 1.5 | 0.1M LA | 2.6 mg/mL Red 40 Lake powder<br>2.5 mg/mL Venetian Red pigment<br>0.70 mg/mL Lac dye powder (Rublev)<br>151 mL/mL glycerol<br>0.98 mL/mL Triton ™ X-100 |
| B2.6-14 | LMW | 1.5 | 0.1M LA | 2.6 mg/mL Red 40 Lake powder<br>1.0 mg/mL iron oxide pigment (Kremer)<br>0.70 mg/mL Lac dye powder (Rublev)<br>15 µL/mL glycerol<br>0.98 µL/mL Triton ™ X-100 |
| B2.7-1 | LMW | 1.5 | 0.1M LA | 2.6 mg/mL Red 40 Lake powder<br>0.26 mg/mL iron oxide pigment (Kremer)<br>0.43 mg/mL Lac dye powder (Rublev)<br>23 µL/mL glycerol<br>0.23 µL/mL Triton ™ X-100<br>0.1% sodium benzoate |
| B2.7-2 | LMW | 1.5 | 0.1M LA | 5 mg/mL Red 40 Lake powder<br>16 µL/mL Blue 1 Lake powder<br>0.1% sodium benzoate |
| B2.7-3 | LMW | 1.5 | 0.1M LA | 5 mg/mL Red 40 Lake powder<br>27 µg/mL Blue 1 Lake powder<br>0.1% sodium benzoate |
| B2.7-4 | LMW | 1.5 | 0.1M LA | 4.7 mg/mL Red 40 Lake powder<br>0.21 mg/mL titanium dioxide pigment<br>0.1% sodium benzoate |
| B2.7-5 | LMW | 1.5 | 0.1M LA | 16.6 mg/mL Red 40 Lake powder<br>9.9 µg/mL Blue 1 Lake powder<br>0.1% sodium benzoate |
| B2.7-6 | LMW | 1.5 | 0.1M LA | 10 mg/mL Red 40 Lake powder<br>9.9 µg/mL Blue 1 Lake powder<br>0.1% sodium benzoate |
| B2.7-7 | LMW | 1.5 | 0.1M LA | 16.9 mg/mL Red 40 Lake powder<br>9.9 µg/mL Blue 1 Lake powder<br>0.1% sodium benzoate |
| B2.7-8 | LMW* | 1 | 0.1M LA | 10 mg/ml Red 40 Lake powder<br>0.3 mg/ml Blue 1 Lake |
| B2.7-9 | LMW | 1.5 | 0.1M LA | 10 mg/ml Red 40 Lake |
| B2.7-10 | Sodium Alginate | 1.5 | DI Water | 10 mg/ml Red 40 Lake |
| B2.7-11 | Sodium Alginate | 0.5 | DI Water | 10 mg/ml Red 40 Lake |
| B2.7-12 | LMW + Sodium Alginate | (1.5 LMW)<br>(0.5 SA) | 0.1M LA | 0.01 g/ml Red 40 Lake |
| B2.7-13 | LMW | 1.5 | 0.1M LA | 16.5 mg/ml Red 40 Lake<br>0.01 mg/ml Blue Lake |
| B2.7-14 | Sodium Alginate | 1 | DI Water | 16.6 mg/ml Red 40 Lake Dye<br>0.01 mg/ml Blue Lake Dye |
| B2.7-15 | Sodium Alginate | 0.5 | DI Water | 16.6 mg/ml Red 40 Lake Dye<br>0.01 mg/ml Blue Lake Dye |
| B2.7-16 | Sodium Alginate | 1 | DI Water | 16.5 mg/ml Red 40 Lake Dye |
| B2.7-17 | Sodium Alginate | 0.5 | DI Water | 10 mg/ml Red 40 Lake Dye<br>0.01 mg/ml Blue Lake |
| B2.8-1 | LMW | 1.5 | 0.1M LA | 16.9 mg/mL Red 40 Lake Powder<br>9.9 µg/mL Blue 1 Lake powder<br>0.1% Triton X-100<br>0.1% Sodium Benzoate |
| B2.8-2 | Sodium Alginate | 0.5 | DI Water | 16.7 mg/mL Red 40 Lake Dye |
| B2.8-3 | LMW | 1.5 | 0.1M LA | 16.8 mg/mL Red 40 Lake powder<br>9.8 µg/mL Blue 1 Lake powder<br>0.1% Triton X-100<br>0.1% Sodium Benzoate<br>1% Glycerol |
| B2.8-4 | LMW | 1.5 | 0.095M LA | 16.2 mg/mL Red 40 Lake powder<br>9.43 µg/mL Blue 1 Lake powder<br>0.095% Triton X-100<br>0.095% Sodium Benzoate<br>5% Glycerol |

TABLE 1-continued

Blood Simulant Formulations

| # | Gellable Component | | | Colorant |
|---|---|---|---|---|
| | type | Conc. (%) | solvent | Type and concentration |
| B2.8-5 | LMW | 1.5 | 0.09M LA | 15.5 mg/mL Red 40 Lake powder<br>9.0 µg/mL Blue 1 Lake powder<br>0.09% Triton X-100<br>0.091% Sodium Benzoate<br>10% Glycerol |
| B2.8-6 | LMW | 1.5 | 0.09M LA | 15.5 mg/mL Red 40 Lake powder<br>9.0 µg/mL Blue 1 Lake powder<br>0.091% Sodium Benzoate<br>10% Glycerol |
| B2.8-7 | LMW | 1.5 | 0.09M LA | 15.5 mg/mL Red 40 Lake powder<br>9.0 µg/mL Blue 1 Lake powder<br>0.091% Sodium Benzoate |
| B2.8-8 | LMW* | 1.5 | 0.09M LA | 16.9 mg/mL Red 40 Lake powder<br>9.9 µg/mL Blue 1 Lake powder<br>0.091% Sodium Benzoate<br>0.1% Triton X-100 |
| B2.8-9 | LMW* | 1.5 | 0.09M LA | 16.9 mg/mL Red 40 Lake powder<br>9.9 µg/mL Blue 1 Lake powde<br>0.091% Sodium Benzoate |
| B2.8-10 | LMW | 1.5 | 0.1M LA | 16.9 mg/mL Red 40 Lake Powder<br>9.9 µg/mL Blue 1 Lake powder<br>0.1% Triton X-100<br>0.1% Sodium Benzoate<br>0.0008% 1-octene-3-one |
| B2.9-1 | LMW | 1.5 | 0.1M Lactic Acid (as 1.5% PURAC Powder 60) | 16.9 mg/mL Red 40 Lake powder<br>9.9 µg/mL Blue 1 Lake powder<br>0.1% sodium benzoate |
| B2.10-1 | Sodium Alginate | 0.5 | DI Water | 16.6 mg/mL Red 40 Lake powder<br>0.13% Triton X-100<br>16.6 µg/mL Blue 1 Lake powder |
| B2.10-2 | Sodium Alginate | 0.5 | DI Water | 9.9 mg/mL Red 40 Lake powder<br>49.3 µg/mL Blue 1 Lake powder<br>0.1% Triton X-100 |
| B2.10-3 | Sodium Alginate | 0.255 | DI Water | 29.7 mg/mL Red 40 Lake powder<br>33 µg/mL Blue 1 Lake powder<br>0.6% Triton X-100<br>957-69 |
| B2.10-4 | Sodium Alginate | 0.235 | DI Water | 5.7% Simulaids Blood Powder<br>2.4 mg/mL Red 40 Lake powder |
| B2.10-5 | Sodium Alginate | 0.5 | DI Water (pH 4.0 with~40 HL HCL) | 9.9 mg/mL Red 40 Lake powder<br>49.3 mg/mL Blue 1 Lake powder<br>0.1% Triton X-100 |
| B2.10-6 | Sodium Alginate | 0.235 | DI Water | 5.7% Simulaids Blood Powder<br>3.1 mg/mL Red 40 Lake powder |
| B2.10-7 | Sodium Alginate | 0.25 | DI Water | 2.5 mg/mL Carminic Acid |
| B2.10-8 | Sodium Alginate | 0.25 | DI Water | 2.5 mg/mL Carminic Acid<br>1% Dispersant 1150 |
| B2.10-9 | Sodium Alginate | 0.25 | DI Water | 2.5 mg/mL Carminic Acid<br>0.5% Dispersant 1150 |
| B2.10-10 | Sodium Alginate | 0.25 | DI Water | 10 mg/mL Carminic Acid<br>33.3 µg/mL Blue 1 Lake<br>0.1% Dispersant 1150 |
| B2.10-11 | Sodium Alginate | 0.25 | DI Water | 10 mg/mL Carminic Acid<br>66.6 µg/mL Blue 1 Lake<br>0.2% Dispersant 1150 |
| B2.10-12 | Sodium Alginate | 0.25 | DI Water | 10 mg/mL Carminic Acid<br>66.6 µg/mL Blue 1 Lake<br>0.4% Dispersant 1150 |
| B2.10-13 | Sodium Alginate | 0.25 | Simulaids Blood | 66.6 µg/mL Blue 1 Lake<br>0.4% Dispersant 1150<br>2 mg/mL Micronized Iron Oxide Red |
| B2.10-14 | LMW** | 1.45 | 0.1M LA | 0.1% Sodium Benzoate<br>3.2 mg/mL Red 40 Lake<br>Concentrate Mix with LA Red 40 Concentrate |
| B2.10-15 | LMW** | 1.45 | 0.1M LA | 0.1% Sodium Benzoate<br>27.41 mg/mL Red 40 Lake<br>3.23 µg/mL Blue 1 Lake<br>Concentrate mix with LA Dual Dye Concentrate |

TABLE 1-continued

Blood Simulant Formulations

| # | Gellable Component | | | Colorant |
|---|---|---|---|---|
| | type | Conc. (%) | solvent | Type and concentration |
| B2.10-16 | LMW** | 1.45 | 0.097M LA | 0.1% Sodium Benzoate<br>3.2 mg/mL Red 40<br>Concentrate mix with water Red 40 Concentrate |
| B2.10-17 | LMW** | 1.41 | 0.094M LA | 0.09% Sodium Benzoate<br>6.25 mg/mL Red 40 Lake<br>Concentrate mix with water Red 40 Concentrate |
| B2.10-18 | LMW** | 1.41 | 0.094M LA | 0.09% Sodium Benzoate<br>6.25 mg/mL Red 40 Lake<br>31.25 µg/mL Blue 1 Lake<br>Both dyes added as individual water concentrates |
| B2.10-19 | LMW** | 1.41 | 0.094M LA (as 1.5% PURAC Powder 60) | 6.25 mg/mL Red 40 Lake<br>Concentrate mix with water Red 40 concentrate |
| B2.10-20 | LMW** | 1.36 | 0.091M LA | 9.09 mg/mL Red 40 Lake<br>0.09% Sodium benzoate<br>Concentrate mix with water Red 40 concentrate |
| B2.10-21 | LMW** | 1.29 | 0.086M LA | 0.086% Sodium Benzoate<br>14.3 mg/mL Red 40 Lake<br>Concentrate mix with water Red 40 concentrate |
| B2.10-22 | Sodium Alginate | 0.21 | DI Water | 14.3 mg/mL Red 40 Lake<br>Concentrate mix with water Red 40 concentrate<br>BS-946-088B |
| B2.10-23 | LMW** | 1.5 | 0.1M LA | 2% glycerol<br>0.1% sodium benzoate<br>0.1% Disperplast 1150<br>17 mg/mL Red 40 Lake<br>10 µg/mL Blue 1 Lake<br>Concentrated chitosan (Chito B2) and dye concentrate<br>(Dual-LA) mixed to 500 mL. |

**Industrial scale, low molecular weight, crab shell chitosan from Dungeness
*Formulations using chitosan supplied by Dungeness Environmental
Conc: concentration
LMW: low molecular weight
aLMW: autoclaved low molecular weight
AA: acetic acid Example 2A Simulated Hemostatic Dressings For Chitosan-Based Simulation Blood Formulations Different variants of simulated hemostatic dressings were prepared for use with chitosan-based simulated blood formulations as identified in Table 2 below. In general, the gelling agent was absorbed either directly from aqueous solution or from a binder material solution into common commercially available medical gauze products. The gelling agents for chitosan-based formulations include compounds that (1) neutralize the acidic solvent to create a neutral or slightly basic solution in which chitosan is no longer soluble, (2) cause chitosan to precipitate out of the dilute acid solution via ionic complex formation and/or (3) crosslink the chitosan into a highly hydrated clot-like gel. Following absorption of the hemostatic agent, the simulated hemostatic dressings were allowed to dry as noted.

TABLE 2

Simulated Hemostatic Dressings

| | Dressing material | | Crosslinker/complexer | |
|---|---|---|---|---|
| # | brand | Material | material | Drying method |
| D1-1 | Triangular splint bandage | Unknown | 20% NaTPP | 75° C. oven |
| D1-2 | CVS sterile gauze pad | Rayon-polyester | 20% NaTPP | 75° C. oven |
| D1-3 | CVS sterile gauze pad | Rayon-polyester | 5-7 mL 10% Na-TPP | 45 min in 75° C. oven; ambient overnight |
| D1-4 | CVS sterile gauze pad | Rayon-polyester | 5-7 mL 50/50 10% Na-TPP/45% β-GP | 45 min in 75° C. oven; ambient overnight |
| D1-5 | CVS sterile gauze pad | Rayon-polyester | 5-7 mL 50/50 1.5M sodium bicarbonate/45% β-GP | 45 min in 75° C. oven; ambient overnight |
| D1-6 | CVS stretchy rolled gauze | Rayon-polyester | 5-7 mL 10% Na-TPP | 45 min in 75° C. oven; ambient overnight |

TABLE 2-continued

Simulated Hemostatic Dressings

| # | Dressing material brand | Material | Crosslinker/complexer material | Drying method |
|---|---|---|---|---|
| D1-7 | CVS stretchy rolled gauze | Rayon-polyester | 5-7 mL 50/50 10% Na-TPP/45% β-GP | 45 min in 75° C. oven; ambient overnight |
| D1-8 | CVS stretchy rolled gauze | Rayon-polyester | 5-7 mL 50/50 1.5M sodium bicarbonate/45% β-GP | 45 min in 75° C. oven; ambient overnight |
| D1-9 | CVS extra absorbent gauze roll | Rayon-polyester | 5-7 mL 10% Na-TPP | 45 min in 75° C. oven; ambient overnight |
| D1-10 | CVS extra absorbent gauze roll | Rayon-polyester | 5-7 mL 50/50 10% Na-TPP/45% β-GP | 45 min in 75° C. oven; ambient overnight |
| D1-11 | CVS extra absorbent gauze roll | Rayon-polyester | 5-7 mL 50/50 1.5M sodium bicarbonate/45% β-GP | 45 min in 75° C. oven; ambient overnight |
| D1-12 | Kerlix gauze roll | Cotton | 5-7 mL 10% Na-TPP | 45 min in 75° C. oven; ambient overnight |
| D1-13 | Kerlix gauze roll | Cotton | 5-7 mL 50/50 10% Na-TPP/45% β-GP | 45 min in 75° C. oven; ambient overnight |
| D1-14 | Kerlix gauze roll | Cotton | 5-7 mL 50/50 1.5M sodium bicarbonate/45% β-GP | 45 min in 75° C. oven; ambient overnight |
| D2-1 | CVS sterile gauze pad | Rayon-polyester | 3 mL 3% powdered gelatin/5% NaTPP | ambient overnight |
| D2-2 | CVS sterile gauze pad | Rayon-polyester | 3 mL 3% bovine Type B gelatin/5% NaTPP | ambient overnight |
| D3-1 | CVS sterile gauze pad | Rayon-polyester | 0.44 mL/in$^2$ 15% NaTPP | NaTPP dried at 70° C. for 90 min |
| D3-2 | CVS sterile gauze pad | Rayon-polyester | 0.44 mL/in$^2$ 15% NaTPP 0.33 mL/in$^2$ 3% Type B gelatin | NaTPP dried at 70° C. for 90 min gelatin dried in ambient overnight |
| D3-3 | CVS sterile gauze pad | Rayon-polyester | 0.44 mL/in$^2$ 15% NaTPP 0.66 mL/in$^2$ 3% Type B gelatin | NaTPP dried at 70° C. for 90 min gelatin dried in ambient overnight |
| D3-4 | CVS sterile gauze pad | Rayon-polyester | 0.44 mL/in$^2$ 15% NaTPP 0.33 mL/in$^2$ 12% Type B gelatin | NaTPP dried at 70° C. for 90 min gelatin dried in ambient overnight |
| D3-5 | CVS sterile gauze pad | Rayon-polyester | 0.44 mL/in$^2$ 15% NaTPP 0.66 mL/in$^2$ 12% Type B gelatin | NaTPP dried at 70° C. for 90 min gelatin dried in ambient overnight |
| D3-6 | CVS sterile gauze pad | Rayon-polyester | 0.56 mL/in$^2$ 15% NaTPP/20 mg/mL Rose Bengal | Dried at 70° C. for 1 hour |
| D4-1 | CVS sterile gauze pad | Rayon-polyester | 0.67 mL/in$^2$ 20% NaTPP | NaTPP dried at 70-75° C. for 20 min |
| D4-2 | CVS sterile gauze pad | Rayon-polyester | 0.67 mL/in$^2$ 20% NaTPP 0.33 mL/in$^2$ 3% Type A gelatin | NaTPP dried at 70-75° C. for 20 min gelatin dried in ambient overnight |
| D5-1 | CVS sterile gauze pad | Rayon-polyester | 0.61 mL/in$^2$ 20% NaTPP in deionized water | Dried at 75° C. in two 10 min increments followed by 1 hour air dry |
| D6-1 | CVS sterile gauze pad | Rayon-polyester | 0.28 mL/in$^2$ 1.5 mg/mL methyl cellulose/150 mg/mL NaTPP in deionized water | Dried at 75° C. followed by 1 hour air dry |
| D2.4-1 | CVS sterile gauze pad | Rayon-polyester | 10% NaTPP/0.5% Type A gelatin Airbrushed, 3 coats | 260° C. heat gun after each coat |
| D2.4-2 | CVS sterile gauze pad | Rayon-polyester | 10% NaTPP/0.5% Type B gelatin Airbrushed, 3 coats | 260° C. heat gun after each coat |
| D2.4-3 | CVS sterile gauze pad | Rayon-polyester | 15% aqueous NaTPP 1% aqueous methylcellulose Sequentially airbrushed, 3 coats each | 260° C. heat gun after each methylcellulose coat |
| D2.4-4 | CVS sterile gauze pad | Rayon-polyester | 15% NaTPP/1% sodium alginate Airbrushed, 3 coats | 575° C. heat gun after each coat |
| D2.4-5 | CVS sterile gauze pad | Rayon-polyester | 15% NaTPP/1% sodium alginate Airbrushed at 55-60 psi, 3 coats | Pulsed 575° C. heat gun after each coat |

TABLE 2-continued

Simulated Hemostatic Dressings

| # | Dressing material brand | Material | Crosslinker/complexer material | Drying method |
|---|---|---|---|---|
| D2.4-6 | CVS sterile gauze pad | Rayon-polyester | 12.5% NaTPP/17% glycerol Airbrushed at 55 psi, 3 coats | Pulsed 575° C. heat gun after each coat |
| D2.6-1 | CVS sterile gauze pad | Rayon-polyester | 15% NaTPP/15% sodium citrate Airbrushed, 3 coats | 330° C. heat gun after each coat |
| D2.6-2 | CVS sterile gauze pad | Rayon-polyester | 22 mg/mL carboxymethyl cellulose/15% NaTPP/ Airbrushed, 3 coats | 330° C. heat gun after each coat |
| D2.6-3 | Inert Combat Gauze ™ substrate | Rayon-polyester | 3.8M citric acid Airbrushed, 2 coats | 330° C. heat gun after each coat |
| D2.6-4 | Inert Combat Gauze ™ substrate | Rayon-polyester | 1.4M Na-citrate Airbrushed, 3 coats | 330° C. heat gun after each coat |
| D2.6-5 | Inert Combat Gauze ™ substrate | Rayon-polyester | 15% NaTPP 1% carboxymethylcellulose Airbrushed in alternating layers, 3 coats each | 330° C. heat gun after each coat |
| D2.6-6 | Inert Combat Gauze ™ substrate | Rayon-polyester | 1.4M Na-citrate Airbrushed, 1 coat | 330° C. heat gun |
| D2.6-7 | Inert Combat Gauze ™ substrate | Rayon-polyester | 15% NaTPP Airbrushed | 330° C. heat gun |
| D2.6-8 | Inert Combat Gauze ™ substrate | Rayon-polyester | 15% NaTPP Airbrushed, 2 coats | 330° C. heat gun after each coat |
| D2.10-1 | Celox ™ gauze | unknown | 15% NaTPP Soaked, 30 seconds | Air dried overnight |

NaTPP: sodium tripolyphosphate
β-GP: β-glycerophosphate

Example 2B

Simulated Hemostatic Dressings For Alginate-Based Simulation Blood Formulations

Variants of simulated hemostatic dressings prepared for use with alginate-based simulated blood formulations were prepared identically to the variants described above in Example 2A for chitosan-based blood simulant formulations, except that the gelling agent was calcium chloride. One method of absorbing calcium chloride onto the gauze substrates was to immerse the gauze into 0.1 M-1 M aqueous calcium chloride solution for 1 minute, followed by drying. The preferred calcium chloride solution concentration is 0.25 M-0.5 M.

Example 3

Simulated Hemostatic Powders

Different variants of simulated hemostatic powders were prepared as identified in Table 3 below. Gelling agent powders were either used as-received or were mixed into a slurry with chitosan, dried and collected into a powder.

TABLE 3

| # | Material(s) | Description |
|---|---|---|
| P1-1 | NaTPP | As-received powder |
| P1-2 | β-GP | As-received powder |

TABLE 3-continued

| # | Material(s) | Description |
|---|---|---|
| P4-1 | NaTPP chitosan | 2.5 g LMW chitosan mixed with 15 mL of 15% NaTPP in deionized H$_2$O; spread flat and dried overnight at 70° C. |
| P4-2 | NaTPP chitosan | 1 g HMW chitosan mixed with 15 mL of 20% NaTPP in deionized H$_2$O; spread flat and dried overnight at 70° C. |

Example 4

Quantitative Color Approximation 20 mL of each simulated blood sample that was investigated for quantitative color approximation were swirled vigorously and poured into a 9 cm diameter glass Petri dish. To photograph the samples, a white soft box lighting tent was used to aid in reducing reflection glare and to provide even lighting conditions. Sample dishes were placed on a piece of white, plastic-backed absorbent paper to capture any accidental spills. Photographs were taken with a Nikon D90 D-SLR camera using a remote Nikon SB-800 Speedlight flash with factory diffuser cap. The flash was placed 6 inches to the right of the Petri dish and was triggered remotely using the Nikon D90's integrated slave flash system that utilizes the SB-800 Speedlight's onboard optical sensor. The camera was set to its manual operation setting, the f-stop was set to f/5.3 and shutter speed was set to 1/40 of a second. A Nikkor AF-S DX 18-105 mm f/3.5-5.6G ED VR lens was used to capture the images. The focal length of the lens was set to 75-80 mm to capture all images. The camera's white balance settings were custom calibrated to the lighting tent by photographing the empty space and allowing the camera to set the white background as a baseline.

The images were cropped to 500×500 pixels using ADOBE® Photoshop 6 software. The Petri dish images were then masked with a green image layer containing nine 5×5 pixel square holes. Using the color sampling tool of the ADOBE® Photoshop software, a 3×3 pixel sized sample was taken from the underlying Petri dish image of the simulated blood solutions. The color sampling tool was used to assay a 3×3 pixel square and average the RGB values for the sample area. The RGB values were recorded for each of the 9 sampling areas and the values were averaged.

Once the average RGB values were established, a pure RGB color was created from the results (average values were rounded to the nearest whole number). Using ADOBE® Photoshop software, a new 500×500 pixel image was created and filled with a custom color made using the average RGB values from each simulant sample. This new, solid color recreated the average color value of the surface of the blood simulant and allowed for easy visual comparison of color ranges of simulants versus human whole blood. The RGB images were saved as BMP (Bitmap) file type to minimize data compression and color loss. The pure RGB color values of each sample tested are shown in Table 4 below. The samples are listed in order of similarity to human whole blood based on the root mean square error of the RGB values relative to those of human whole blood. The results show that the color of the simulated blood samples of the present invention compare very well to that of human whole blood.

TABLE 4

| Sample | R | G | B | RMS | RMSE |
| --- | --- | --- | --- | --- | --- |
| Blood | 89 ± 7 | 36 ± 3 | 41 ± 9 | 105 | 0 |
| B2.4-1 | 95 | 36 | 31 | 106 | 1 |
| B2.6-5 | 96 | 35 | 32 | 107 | 2 |
| B2.6-9 | 93 | 31 | 29 | 102 | 3 |
| B5-3 | 98 | 44 | 43 | 116 | 11 |
| B2.4-2 | 108 | 36 | 29 | 117 | 12 |
| B2.4 | 101 | 44 | 44 | 119 | 14 |
| B2.6-4 | 106 | 41 | 36 | 119 | 14 |
| B2.6-1 | 110 | 35 | 32 | 120 | 15 |
| B4-6 | 67 | 39 | 40 | 87 | 18 |
| B2.3-3 | 115 | 33 | 33 | 124 | 19 |
| B5-5 | 50 | 40 | 28 | 70 | 35 |
| B2.6-3 | 132 | 40 | 38 | 143 | 38 |
| B2.3-1 | 143 | 36 | 30 | 150 | 46 |
| B2.3-7 | 149 | 37 | 34 | 157 | 52 |
| B2.3-2 | 151 | 35 | 30 | 158 | 53 |
| B2.1-1 | 157 | 45 | 41 | 168 | 63 |
| B2.3-6 | 161 | 37 | 33 | 168 | 63 |
| B2.2-4 | 178 | 42 | 36 | 186 | 81 |
| B2.2-1 | 199 | 42 | 36 | 207 | 102 |
| B2.2-2 | 206 | 44 | 37 | 214 | 109 |
| B4-1 | 181 | 92 | 105 | 229 | 124 |

"Blood" = human whole blood;
RMS = root mean square of RGB values;
RMSE = root mean square error relative to RGB values for three human whole blood.

Example 5

Viscosity Testing

The kinematic viscosity of simulated blood formulations and human whole blood was determined using a Cannon-Fenske 100 routine viscometer. Fluid was drawn into the viscometer and the time required for the fluid meniscus to flow through a marked chamber was recorded. 3 efflux times were recorded and averaged for each sample. Kinematic viscosity was determined by multiplying the mean efflux time in seconds by the viscometer constant. Simulated blood formulations were tested at 22° C. (viscometer constant=0.01633) and human whole blood was tested at 37° C. (viscometer constant=0.01631). The results, shown in Table 5 below, indicate that the viscosity of the simulated blood formulations compare very well to that of human whole blood, especially formulation B4-7.

TABLE 5

| Sample | Mean efflux time (seconds) | Kinematic viscosity (cStokes) |
| --- | --- | --- |
| Human whole blood (37° C.) | 351 ± 6 | 5.72 |
| B4-7 | 340 ± 5 | 5.56 |
| B5-3 | 470 ± 10 | 7.68 |
| B4-2 | 553 ± 16 | 9.03 |
| B5-5 | 832 ± 1 | 13.6 |
| B5-4 | 951 ± 10 | 15.5 |

Example 6

Flow Testing

Comparative testing of the rates at which simulated blood formulations and whole blood flow through tubing was performed so as to determine the realism of simulated blood formulations when used in trauma training mannequins. A 50 mL syringe barrel was filled with either a sample of simulated blood at room temperature (20° C.) or human whole blood at human body temperature (37° C.). Human whole blood was tested at several different time points after draw to determine if "age" was a factor. A syringe barrel was attached to a 24 in length of tubing and the assembly was suspended from a clamp with the syringe barrel open to the atmosphere. The time required for 50 mL of simulated or actual human whole blood to flow though tubing of varying inner diameters (1/16", 1/8" and 1/4") was recorded. The tubing was wetted with 50 mL of simulated blood formulation or whole human blood prior to testing. Samples were run in triplicate.

The results, shown in Table 6 below, indicate that it took significantly more time for all of the simulated blood formulations to flow through the system than it did for the human whole blood, regardless of age. Of the simulated blood formulations tested in this way, the one with flow-through time closest to that of human whole blood was formulation B4-2.

TABLE 6

| | Flow Time (sec) | | | | | | |
| --- | --- | --- | --- | --- | --- | --- | --- |
| | Simulated Blood Formulations | | | | Human Whole Blood | | |
| Tubing ID | B3-7 | B4-1 | B4-2 | B4-5 | 4 day old | 10 day old | 23 day old |
| 1/16" | 650 ± 26 | 744 ± 23 | 300 ± 6 | 596 ± 6 | 94 ± 1 | — | 144 ± 18 |
| 1/8" | 52 ± 0 | 64 ± 2 | 26 ± 1 | 48 ± 1 | 12 ± 2 | 12 ± 0 | 14 ± 1 |
| 1/4" | 2 ± 1 | 3 ± 0 | 1 ± 0 | 2 ± 0 | 1 ± 0 | — | 1 ± 0 |

Values are means ± standard deviations (n = 3)

Example 7

Fabric Stain Testing

Swatches of 50/50 Nylon/Cotton universal camouflage Army Combat Uniform (ACU) fabric were used to test the staining properties of several of simulated blood formulations. This study was designed to mimic spilling of blood simulant on the uniform of a trainee during use. Prior to testing, the ACU fabric was washed once in a household washing machine on a cold/cold standard cycle with 50 mL of WISK® High Efficiency detergent and hung dry prior to testing. Staining was tested after exposures of five minutes and 24 hours.

Five Minute Exposure

A 5 minute exposure staining test was carried out using 4 in.×5 in. swatches of ACU fabric. A 5 mL sample of simulated blood was placed onto each ACU fabric sample and allowed to soak in for 5 minutes. The ACU fabric swatches were then scrubbed by hand under luke-warm (25-30° C.) water for 2-3 minutes by folding them over and rubbing the ACU fabric together followed by soaking the swatch in the running water and wringing it out by hand. No detergent was used to clean the ACU fabric. The swatch samples were hung on a line in the laboratory and were left to air dry overnight. The dried swatches were examined for staining and photographed. The results of the testing are shown in FIG. 1.

Most of the simulated blood formulations left no stain. Two formulations, B5-3 and B5-4, left very light stains that could only be observed in the lighter color portions of the camouflage pattern. It is unclear why B5-3 and B5-4 performed differently than the others, except that they both contained relatively high quinacridone red pigment. Formulations B6-4 and B6-6 also contained quinacridone, but were also formulated with glycerol. It is believed that glycerol may maintain higher moisture content in stained fabric and thereby aid in stain removal. The glycerol-containing formulations also appeared more like human blood when first applied to the ACU fabric.

24 Hour Exposure

The 24 hour exposure staining test was carried out using 8 in.×8 in. swatches of ACU fabric. Each ACU fabric sample was stained with 5 mL of human whole blood or blood simulant, which was then allowed to soak into the fabric for 24 hours on the benchtop. Notes and observations were made during the staining procedure to compare the interaction of the blood simulants with the ACU fabric as compared to human whole blood. After 24 hours, the ACU fabric swatches were washed in a FRIGIDAIRE® Super Capacity, Heavy Duty Tumble Action household washing machine on warm/warm 1 hour wash setting with approximately 50 mL of TIDE® High Efficiency (HE) Detergent. The washed swatch samples were hung to dry overnight. The dried swatches were examined for staining and photographed. The interaction observations and stain removal results are shown in FIGS. 2A and 2B.

While whole blood was laundered out completely most of the simulated blood formulations left a visible stain behind. The two blood simulants that were laundered completely were the glycerol-containing formulations, B6-3 and B6-5. In addition, the glycerol-containing formulations presented and persisted on the surface of the ACU fabric with a vibrant red color much closer to that of human whole blood than all non-glycerol containing formulations.

Example 8

Tackiness/Material Adhesion Testing

The tackiness or adhesive properties of several simulated blood formulations were evaluated relative to that of citrated human whole blood. Coupons made from glass, wood, polyurethane rubber and medical silicone were lowered vertically into blood simulant or human whole blood (at 37° C.) and immersed at a 5 cm depth for 30 seconds. The coupons were quickly removed and any solution that dripped from the coupon was collected and weighed. Samples were tested in triplicate.

The results show that citrated human whole blood was significantly more tacky than all of the blood simulant formulations tested. Although the differences between most means were not statistically significant, the trends are interesting. Formulation B5-4, which tended to be the most tacky formulation tested, contained only pigments. Formulations B5-4 and B6-6 had identical chitosan and pigment packages, but B6-6 contained glycerol and B5-4 did not. Formulations B6-7 and B6-8 incorporated methyl cellulose and the chitosan was present at a higher concentration. Interestingly, although both glycerol and methyl cellulose were added, in part, to increase the stickiness of the blood simulants, they actually had the opposite effect. Formulation B3-7 contained several pigments and 4× concentrated natural cherry juice and was generally intermediate in tackiness between B5-4, which tended to be more tacky and B6-6, B6-7 and B6-8, which tended to be less tacky. Visual inspection of the test coupons suggested only slight qualitative differences in the interaction between the glycerol- or methyl cellulose-containing prototype blood simulants and the different materials.

Example 9

Shelf Life Testing

Simulated blood for trauma training modules must maintain its properties when inventoried and stored. Samples of blood simulant formulations B4-1, B4-2, B4-5 and B5-5 were selected for "accelerated" shelf life testing that consisted of regular cycling between high and low temperature extremes. 30 mL of each solution were placed in a small glass bottle and sealed to prevent evaporation. The samples were placed in a 50° C. oven and were moved to a 4° C. refrigerator after 24 hours. The samples were alternated between 50° C. and 4° C. every 24 hours during the week and were stored at room temperature over the weekends. The test was conducted for four weeks.

The samples were photographed before testing began and at the conclusion of the four week study. The samples were also observed when transported from the refrigerator to the incubator. Initially, all formulations exhibited some pigment settling, but the pigment could be re-suspended easily with vigorous swirling. No color loss was observed despite the pigment settling. After 2 weeks, formulations B4-5 and B5-5 become more viscous. After 4 weeks, both formulations were "gelatinous," having the consistency of jelly. Both of these formulations contained concentrated cherry juice. Formulations B4-1 and B4-2, which did not contain cherry juice extract, did not undergo an increase in viscosity during the four week test.

Example 11A

Benchtop Shelf Life Studies of Viscosity Change—Chitosan

Figure 3:
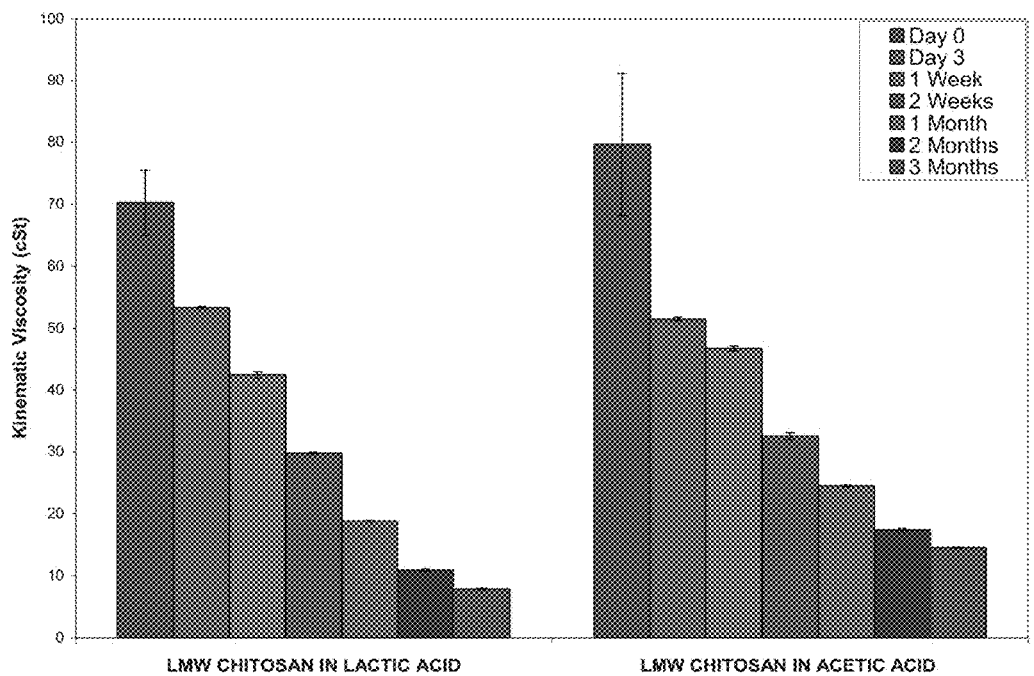
FIG. 3 is a graph of kinematic viscosity (cSt) over time for 1.5% LMW Chitosan (Sigma) in 0.1 M lactic and acetic acid solutions, where the values are mean±standard deviation (n=3) for the benchtop shelf life studies conducted according to Example 11A.

In order to analyze the effects of acid hydrolysis and decreased degree of deacetylation of chitosan in acidic solution over time, changes in kinematic viscosity were monitored over time. Samples of 1.5 wt % low molecular weight chitosan in 0.1M lactic acid or 0.1 M acetic acid were stored at room temperature and viscosity was obtained using a size 100 Fenske viscometer at various time points. The results are shown graphically in FIG. 3.

The results indicate a decrease in kinematic viscosity over time. For both samples, viscosity decreased for the entire 3 month testing period with a kinematic viscosity of approximately 10 to 15 cSt for both solutions at 3 months. Other results have shown that chitosan solution that had remained on the shelf for up to six months still exhibited good gel clot formation when in contact with NaTPP, despite the decrease in solution viscosity. Acid hydrolysis on the shelf may actually be a benefit since the viscosity of blood is very low (approximately 3 cSt).

Example 11B

Benchtop Shelf Life Studies of Viscosity Change—Alginate

Figure 4:
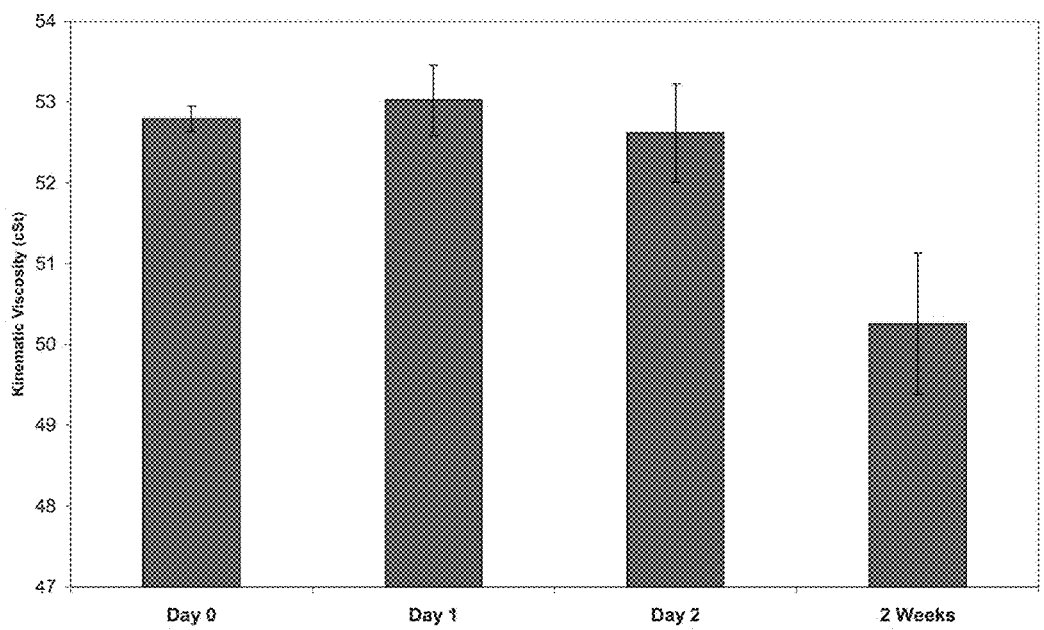
FIG. 4 is a graph of kinematic viscosity (cSt) over time for 0.5% alginate in deionized water solutions where values are mean±standard deviation (n=3) for the benchtop shelf life studies conducted according to Example 11B.

The shelf life behavior of alginate-based blood simulants has also been studied by monitoring changes in kinematic viscosity for a solution of 0.5% alginate in deionized water. The solution has been tested out to two weeks. The results are shown in FIG. 4 and show that the viscosity remained stable for at least two days but then exhibited a statistically significant decrease at two weeks.

Example 12

Static Assessment of Simulated Blood Formulations and Simulated Hemostatic Dressings Static testing of various combinations of simulated blood formulation and simulated hemostatic dressing was performed. Static testing involved immersing 3 in.×1 in. test strips of the simulated hemostatic dressing materials into a simulated blood formulation. The test strips of dressing materials were observed to determine the formation of gel "coagulum." It was observed that dressings impregnated with sodium tripolyphosphate (Na-TPP) provided the most realistic "clot" formation for chitosan-based blood simulant formulations. Comparably realistic results were obtained with alginate-based blood simulant formulations comprising 0.5 wt % sodium alginate and dressings impregnated with calcium chloride.

Example 13

Static Assessment of Simulated Hemostatic Powder

Testing of potential simulated hemostatic powder was conducted using an uncolored stock solution of 2% LMW chitosan in 0.1 M acetic acid. 50 mg of sodium tripolyphosphate (Na-TPP) powder (simulated hemostatic powder P1-1) was added to approximately 5 mL of the LMW chitosan solution in a glass Petri dish. Without active mixing, the sodium tripolyphosphate powder did not readily dissolve or disperse into the chitosan solution after five minutes. Instead, a small ring of crosslinked gel formed around the edge of the powder. When the sodium tripolyphosphate salt was mixed into the chitosan with a spatula, the powder began to cross-link the chitosan and form a hazy, opaque gel.

The same experiment was performed using β-glycerophosphate powder (P1-2). The β-glycerophosphate was added on top of approximately 5 mL LMW chitosan solution. When the salt was mixed into the chitosan solution, crosslinking was not rapid. The solution was left for 10 minutes but no cross-linked gels appeared to form. The mixture was slightly hazy but did not form a white gel as with the sodium tripolyphosphate.

Two additional hemostatic powder simulants were tested that consisted of sodium tripolyphosphate/chitosan powder blends. The first hemostatic powder simulant (P4-1) was prepared by mixing 2.5 g of stock low molecular weight chitosan powder with 15 mL of 15% sodium tripolyphosphate in deionized water. The second simulated hemostatic powder (P4-2) was prepared by mixing 1 g of stock high molecular weight chitosan flakes with 15 mL of 20% sodium tripolyphosphate in deionized water. Both slurries were spread flat onto a glass Petri dish and dried overnight at 70° C.

After the slurries had dried, they were scraped from the glass dishes. The high molecular weight P4-2 flakes were easier to remove than the low molecular weight P4-1 powder. Both samples appeared to have a large amount of sodium tripolyphosphate salt settled on the bottom of the dish, creating a lower layer of salt and an upper layer of chitosan. The layers were bound to each other well.

To test the clotting ability of simulated hemostatic powders P4-1 and P4-2, 0.4 g of each was sprinkled on top of approximately 30 mL of 2% deacetylated low molecular weight chitosan in 0.1 M acetic acid. The powders were allowed interact statically with the chitosan solution for 10 minutes. After 10 minutes both powders had formed a thick, white gel layer across the top of the chitosan solution. When the gels were lifted up, both exhibited good cohesion and were removed in one large piece.

Example 14

Quantitative Assessment of Interaction with Dressings Under Pressure

A system to test blood simulant flow through treated gauze under pressure included a 60 mL syringe held vertically with a clamp and ring stand. A 24 in long piece of ⅛ in inner diameter silicone tubing was attached to the nozzle of the syringe. The barb fitting of a custom pressure plug was attached to a pressurized tank of nitrogen. Using a plastic hemostat to pinch the ⅛ in tubing closed, 25-50 mL of blood simulant was added to the open syringe. The syringe was either left open or the pressure plug was inserted into the open end of the syringe and the nitrogen tank was opened. When the pressure plug was used, an inline pressure regulator was used to maintain the nitrogen gas pressure entering the syringe at 2 psi.

One or two plys of simulated dressing D5-1 or untreated gauze measuring 1.5 in ×1.5 in were folded over the end of the ⅛ in tubing and secured with a zip tie. When the plastic hemostat was released, the pressurized blood simulant flowed through the tubing (at approximate human arterial pressure when set to 2 psi) and interacted with the treated or untreated dressing at the end of the tube.

The results of the flow testing are summarized in FIGS. 5A and 5B. When tested under 2 psi pressure, 50 mL of blood simulant B3-7 drained rapidly through both the untreated gauze and dressing D5-1, with little or no difference. When the untreated gauze samples were examined, however, they had not absorbed much of the blood simulant and what was absorbed was less viscous and spread over most of the gauze surface. When the D5-1 hemostatic dressing simulant was examined, a much more concentrated gel had formed on the dressing surface.

When the blood simulant solution was gravity fed (open to atmosphere), performance differences were easier to discern. When an untreated piece of gauze was placed over the drain tube, the 50 mL volume of B3-7 emptied in 27 seconds. When simulated hemostatic dressing D5-1 was used, the 50 mL volume emptied in 1 minute 24 seconds. After 20 seconds, the flow through D5-1 slowed to a drip whereas the untreated gauze drained consistently with no slowing of flow rate. Again, the blood simulant did not adhere to the untreated gauze whereas a larger gel had formed on the surface of the D5-1 dressing material.

The next two experiments involved blood simulants B3-1 and B5-6, which are identical except for the molecular weight and degree of deacetylation of the chitosan (B3-1 has non-deacetylated low molecular weight chitosan and B5-6 has deacetylated medium molecular weight chitosan). When 35 mL of each was allowed to drain under 2 psi, it took 46 seconds for the B3-1 and 11 seconds for the B5-6. When the D5-1 dressing material was examined, there was a very small piece of dark red gel "clot" formed from B3-1 and only a very thin gel layer from B5-6.

The next set of experiments was similar. When 35 mL of blood simulant B5-3 (75 minute autoclaved low molecular weight chitosan) was tested against 2 plys of D5-1 under 2 psi, flow through the dressing material slowed after 30 seconds and stopped after 2-3 minutes. Although 2 psi pressure was maintained behind the solution for 5 minutes, no further flow was noted. Small gels were observed in the catch beaker. A large, gel "clot" formed on the outer surface of the gauze while it was still attached to the tubing and a large gel "clot" was also formed on the inside surface of the D5-1 dressing material. The gel was large enough to effectively "glue" the two pieces of gauze together. When simulated blood formulation B5-7 was used (B5-7 is identical to B5-3, except with deacetylated medium molecular weight chitosan) the result was nearly identical except that the "clots" were less substantial than with B5-3.

In a final test, simulated blood formulation B5-4 (75 minute autoclaved LMW chitosan) and B5-8 (deacetylated MMW chitosan), which had higher chitosan and acetic acid concentrations than the previous four blood simulants, were investigated. When 25 mL of B5-4 was used, the solution evacuated the syringe in 1 min and 10 seconds. No stoppage of flow was observed. Very large gels formed in the catch beaker. Gel "clots" formed on the outer surface of the gauze while it was still attached to the tubing. A medium sized gel "clot" formed on the inside surface of the treated gauze at the site where the tubing directly touched the gauze. The large gel that formed in the catch beaker was very robust and dense but was light pink in color. When 25 mL of B5-8 was used, flow through the D5-1 dressing material slowed after 30 seconds and stopped after 2-3 minutes. 2 psi pressure was maintained behind the solution for 5 minutes, but no further flow was noted. Approximately half of the solution flowed through the system before flow was stopped. Small gels were observed in the catch beaker and a medium sized gel "clot" formed on the inside surface of the dressing at the site where the tubing touched it directly. The gel was more localized than with the B5-4 simulant.

Example 15

Mannequin and Wound Model Testing

Simulated blood formulations B5-4, B6-1, B6-2, B2.5-7, B2.5-8, B2.5-9, B2.5-10, B2.6-9 and B2.6-11 were evaluated for performance characteristics using reservoirs, pumping systems and simulated wound beds representative of those used in the TRAUMA F/X™ simulator (Kforce Government Solutions, Inc.).

Preliminary Flow Loop and Pump Testing

Initial testing of the simulated blood formulations included running 500 mL of blood simulant B5-4 through a circulating flow loop powered by an electronically regulated diaphragm pump system. The temperature of the pump was monitored with an infrared thermometer to observe any overheating conditions. A second system circulating a standard blood simulant (Kforce Government Solutions, Inc.) was run at the same time. Although simulant B5-4 was more viscous than the standard commercial blood simulant, it flowed through the system easily during the course of the experiment. The external temperature of the diaphragm pump used with the simulant B5-4 increased to 32° C. An identical pump used with a water-based solution containing remnants of the standard blood simulant was also increased to 30-32° C.

The next level of testing involved pumping of each simulant through the MATT pump into a waste collection jar for 30 seconds, 1 minute, and 10 minutes. Each system was flushed with water prior to testing and then again afterwards. The pressure of pumping was the same as that used in the mannequin itself, approximately 12 pounds per square inch (psi). The pump systems were monitored for problems with simulant flow, leakage, or pressure. No problems were found for any of the six simulants. Only two new simulants were tested this quarter (four were tested previously in September). Both simulant B2.6-9 (a 1.5% LMW chitosan in 0.1 M lactic acid with dyes and surfactants present) and B2.6-11 (same 1.5% LMW chitosan in 0.1 M lactic acid with different dye package) passed this testing with no complications, clogging, or other issues.

Blood simulants were then tested in long term Level 2 pump testing using automated pumps and sensors that were monitored remotely. The pumps were run continuously with recirculation of the blood simulant and monitored for leakage, temperature, and blood simulant flow. Both systems were observed to run at a pump temperature nearly identical to a water control, indicating no issues with longer term pumping of the simulant. There were no complications observed in Level 2 testing for blood simulant formulations B2.5-7, B2.5-8, B2.5-9, B2.5-10, B2.6-9 or B2.6-11. Blood simulant B2.6-9 was run for a total of 419.5 hours and B2.6-11 for 512 hours before it was determined to switch them (along with the other four simulants discussed below) over to the next level of testing.

The next level of pump testing was performed on 6 blood simulants: B2.6-9, B2.6-11, B2.5-7, B2.5-8, B2.5-9, and B2.5-10. A recirculating pump system. The simulant was allowed to pump for 24 hours and the system was then turned off. The amount of time the system remained dormant (with blood simulant left stagnant within the system during this time) was allowed to increase from 24 to 48 to 72 hours and beyond. This culminated in a 5 day shut-off and an 11 day. After system dormancy, the pump was again turned on and allowed to run continuously for 24 hours. Results indicated that failure occurred for all simulant systems at either 5 or 11 days of dormancy. All 6 failures were caused either directly or indirectly by a clogged pump solenoid.

As a result of solenoid clogging and failure, two pumps failed indirectly. This is due to pumps trying to push fluids through frozen solenoids that have completely clogged. When the pump was disassembled, no clogs were found, indicating that the solenoid design is the critical design flaw for long term stagnation of the blood simulant. The results of this testing also indicates that simulant flushing should occur immediately after use.

Hemorrhage Model Blood Simulant Testing 500 mL of blood simulant B5-4 was loaded into a reservoir and fed into a femoral artery hemorrhage mannequin model (Kforce Government Solutions, Inc.) using a pumping system. The wound bed was allowed to fill with blood simulant for approximately 10 seconds before two 3 in×3 in pieces of simulated hemostatic dressing D5-1 were placed inside the wound directly against the silicone tube feeding the simulated blood into the model. Direct pressure was applied to the wound to simulate battlefield treatment of a large hemorrhage. Blood simulant flowed out of the wound area. The simulant looked quite realistic, although the red color was not quite as bright red as whole blood. As pressure was applied to the wound, flow was reduced and the pumping mechanism, by design, automatically shut off. If pressure was released even slightly, the flow would resume.

After approximately 2 minutes, gelatinous clots could be seen forming around the gauze and flowing off of the wound model onto the table. After approximately 5 minutes the treated gauze was saturated with gel "clots". Gel "clots" adhered to the silicone "skin" of the model as well as to the gauze and hands of the operator. The gels were slightly pink and lighter in color than the unreacted simulant. The blood simulant was easily cleaned off the silicone model between tests by rinsing with water and wiping with baby wipes. The experiment was repeated with identical results.

Blood simulant B6-2, 3 pieces of 3 in ×3 in D5-1 simulated hemostatic dressing and 1 package of 4.5 inches wide×4.1 yards long compressed gauze (H&H PriMed™ Compressed Gauze, H&H Associates, Inc., Ordinary, Va.) were used to conduct a "wound packing" test. After the pieces of D5-1 simulated hemostatic dressing were applied directly to the blood simulant supply tube, the untreated compression gauze was used to fully pack the simulated wound. The compression gauze was packed into the wound and pressure was applied to the hemorrhage model to mimic wound packing to stanch hemorrhage in the field. Blood simulant flow was reduced, but not stopped, throughout the 5 minute test. Large "clots" flowed over the sides of the simulated wound model and formed on the surface of the gauze. Because the treated gauze was so compacted into the wound, gel "clot" formation was pressed into the treated and untreated gauze forming a large, solid lump of gel and gauze. The gauze was very dense and hard to the touch. The outside edge of the treated gauze that was in contact with the blood simulant supply tubing was coated with a thick layer of caked pink gel "clot".

The "wound packing" test was repeated with simulated blood formulation B5-4, three 3 in×3 in pieces of simulated hemostatic dressing D5-1, one package of compressed gauze and direct application of pressure as described above. Gel formation in the "wound packing" model with formulation B5-4 was qualitatively identical to that observed with B6-2.

Another "wound packing" test was performed with simulated blood formulation B6-1. Formulation B6-1 is less viscous than both formulations B5-4 and B6-2, and it flowed quickly from the simulated wound bed. The formulation B6-1 had a brown tint and was much darker and more transparent than formulations B5-4 and B6-2. Gel "clot" formation was much less obvious during the testing, probably due to the lower chitosan concentration. A small amount of gel flowed out of the wound bed and a much smaller amount of gel formed on the surface of the D5-1 simulated hemostatic dressing. The gel "clots" that formed were brown in color.

Additional "wound packing" tests were performed with blood simulant formulations B2.5-7, B2.5-8, B2.5-9, B2.5-10, B2.6-9 and B2.6-11 using a different hemorrhage simulator that is fabricated of silicone and designed to mimic a penetrating wound.

For initial appearance evaluation, simulants were pumped into the simulated hemostatic wounds and an NaTPP-loaded hemostatic gauze simulant sample 12 inches long×3 inches long was packed in the "wound" to induce clotting. No damage was done to the "wound" using the simulant or the gauze. Each of the tested formulations flowed into the wound as needed. Gel "clots" were observed to form within seconds of gauze application, and the gauze was held in place for a total of 3 minutes. Simulant formulations B2.6-9 and B2.6-11 were determined to be more visually appropriate than B2.5-7-B2.5-10, and simulant B2.6-11 was judged the most visually realistic based on color, viscosity, and opacity.

A second round of testing involved an identical setup to that above, but utilized blood simulant that had been pumped through recirculating systems for pump failure testing. Only two simulants were tested in this manner, B2.5-8 and B2.5-10. These are both LMW chitosan simulants (1.9% and 1.4%, respectively) that were prepared with 5% glycerol and Napthol red as the pigment. Testing of their clotting ability after continuous pumping and circulation provides general information related to the use of chitosan in the blood simulant. B2.5-8 was recirculated for a total of 88 hours before testing for clotting and appearance as described above. B2.5-10 was pumped for a total of 330 hours before testing. Neither extensively recirculated simulant exhibited a qualitative difference when compared to their intitial testing prior to recirculation. Simulated blood clots were observed to form in the same time frame, and the clot color and texture appeared identical to previous tests. These testing results indicate that flow through the system does not appear to degrade the blood simulant.

Example 16

Skin Irritation Testing

Primary skin irritation studies were performed to assess the irritant and/or corrosive effects of the simulated blood formulations when given as a single dermal administration to white New Zealand rabbits. The study was designed to mimic spilling of blood simulant on the skin of a trainee during use. The design was aggressive, however, in that the blood simulant was not washed off in a time period that would be expected in a training scenario.

The three blood simulant formulations that were investigated in this primary skin irritation study were B3-1, B5-3 and B5-4. Whereas B3-1 only contains chitosan, acetic acid and cherry juice extract, B5-3 and B5-4 contain alizarin crimson, venetian red and quinacridone red pigments and are therefore more likely to be skin irritants. B5-3 also contains cherry juice extract.

Three groups of rabbits, with 3 animals per group, received 0.5 mL doses of the appropriate test or control materials as single dermal applications per test site. There were two test sites per material per animal. One of the test sites for each material was abraded by utilizing the back of a no. 40 clipper blade. The abrasions were sufficiently deep to penetrate the stratum corneum, but not to disturb the derma. The other test site for each material remained intact. The doses were held in contact with the skin under a semi-occlusive binder for an exposure period of 4 hours. Following the exposure period, the binder was removed and the remaining test materials were wiped from the skin using gauze moistened with deionized water followed by dry gauze. Test sites were subsequently examined and scored for dermal irritation for up to 7 days following patch removal.

Irritation was not observed at the abraded sites following dermal administration of blood simulant B3-1. Very slight erythema was observed at 1 intact test site at the 24 and 48 hour scoring intervals. Complete resolution of irritation occurred by the 72 hour scoring interval. No additional dermal changes were noted at the intact or abraded test sites.

Dermal administration of blood simulant B5-3 resulted in very slight erythema at a single intact site at the 1 hour scoring interval. Irritation was not observed at the abraded sites or remaining intact sites at the 1 hour scoring interval. At the 24 hour scoring interval, irritation was noted at all intact and abraded sites, and ranged from very slight to well-defined erythema. Complete resolution of irritation occurred by the Day 7 scoring interval. No additional dermal changes were noted at the intact and abraded test sites.

Administration of blood simulant B5-4 produced very slight to well-defined erythema and very slight edema by the 1 hour scoring interval. Complete resolution of irritation occurred by the day 7 scoring interval. Additional dermal observations included red staining of the test sites. The staining did not affect the ability to score the test sites.

Sodium dodecycl sulfate (SDS) and glycerol were included in the study as positive and negative controls for skin irritation, respectively. Dermal administration of 25% SDS solution resulted in slight to well-defined erythema at the intact and abraded test sites in all animals beginning at the 1 hour scoring interval and continuing through the final observation interval for the groups. Erythema increased to maximized erythema based on the presence of blanching within the test sites covering greater than 50% of the sites. Additional dermal changes including very slight to slight edema, superficial lightening, and desquamation were noted as the study progressed through the Day 7 scoring interval. No irritation was observed at either the intact or abraded glycerol control sites.

Dermal administration of blood simulant formulation B3-1 resulted in the least irritation when compared to formulations B5-3 and B5-4. The irritation resulting from administration of the B5-3 and B5-4 was comparable, although the irritation induced by B5-3 was slightly less than that of B5-4. B5-4 was the only blood simulant tested that resulted in staining of the test sites. The irritation resulting from the administration of 25% SDS solution demonstrated that the study was conducted in a manner that would indicate potential irritation. All blood simulant solutions had less irritation than the SDS-treated sites, as the irritation in the SDS treated sites was still present through day 7 on the animals remaining on study until that interval. Glycerol served as the negative control and resulted in no irritation. This allowed comparison of the blood simulant solutions to a known non-irritating material, and showed that the irritation induced by the blood simulant solutions was minimal and well tolerated by the animals. These results suggest that the simulated blood formulations are unlikely to be skin irritants, especially if they are washed off in a timely fashion.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope thereof.

What is claimed is:

1. A medical training kit to simulate treatment of wound hemorrhage comprising:
   simulated blood component which comprises at least one gellable component selected from the group consisting of chitosan and alginate, and
   a simulated hemostatic component comprising a gelling agent which causes the gellable component to desolubulize, polymerize, complex, precipitate and/or crosslink so as to form a mass of semi-solid or solid material in response to the simulated blood component being brought into contact therewith to thereby simulate blood clotting, wherein
   the gelling agent is at least one selected from the group consisting of sodium tripolyphosphate (NaTPP), calcium salts, β-glycerophospate, sodium carbonate, sodium bicarbonate, sodium citrate, citric acid and Rose Bengal.

2. The medical training kit as in claim 1, wherein the simulated hemostatic component comprises a carrier for the gelling agent.

3. The medical training kit as in claim 2, wherein the carrier is a liquid, fabric, sponge or pouch.

4. The medical training kit as in claim 1, wherein the simulated hemostatic component is in the form of a particulate or liquid.

5. The medical training kit as in claim 1, wherein the simulated blood component is an aqueous acidic solution comprising chitosan as the gellable component, and wherein the simulated hemostatic component comprises sodium tripolyphosphate (NaTPP).

6. The medical training kit as in claim 5, wherein the chitosan is present in the simulated blood component in an amount between about 0.6 to about 2.0 wt. %.

7. The medical training kit as in claim 5, wherein the chitosan has a molecular weight of between about 50,000 Da to about 500,000 Da.

8. The medical training kit as in claim 5, wherein the chitosan is autoclaved at temperatures between about 100 to about 150° C., at pressures of between about 5 to about 25 psi and a time of between about 1 minute to about 90 minutes.

9. The medical training kit as in claim 5, wherein the chitosan has a percent deacetylation value (% DA) of at least about 70%.

10. The medical training kit as in claim 1, wherein the simulated blood component is an aqueous solution comprising sodium alginate as the gellable component, and wherein the simulated hemostatic component comprises calcium chloride.

11. The medical training kit as in claim 10, wherein the sodium alginate is present in the simulated blood component in an amount between about 0.05 to about 2.0 wt. %.

12. The medical training kit as in claim 10, wherein the sodium alginate has a molecular weight of between about 10,000 Da to about 600,000 Da.

13. The medical training kit as in claim 1, wherein the simulated blood component comprises at least one colorant in an amount sufficient to mimic coloration of whole mammalian blood.

14. The medical training kit as in claim 1, wherein the simulated blood component comprises at least one additive selected from the group consisting of viscosity modifiers and tactile agents.

15. The medical training kit as in claim 10, wherein the simulated blood component comprises a cellulosic material as a viscosity modifier.

16. The medical training kit as in claim 10, wherein the component simulated blood comprises glycerol as a tactile agent.

17. The medical training kit as in claim 10, wherein the simulated blood component comprises a scent modifier selected from the group consisting of 1-octen-3-one or metallic additives.

18. The medical training kit as in claim 14, wherein the gellable component in the simulated blood component comprises chitosan, and wherein the gelling agent comprises sodium tripolyphosphate.

19. The medical training kit as in claim 14, wherein the gellable component in the simulated blood component comprises sodium alginate, and wherein the gelling agent comprises calcium chloride.

20. The medical training kit as in claim 18 or 19, wherein the simulated hemostatic component is in the form of a simulated hemostatic dressing comprising a fabric substrate and a gelling agent carried by the fabric substrate.

21. The medical training kit as in claim 20, wherein the gelling agent is present in an amount of between about 10 wt. % to about 80 wt. %, based on the weight of the fabric substrate.

22. The medical training kit as in claim 1, wherein the simulated blood component is in the form of a dry powder or a concentrated liquid, gel or paste which when mixed with a liquid solvent forms a liquid simulated blood.

23. A gellable simulated liquid blood which comprises:
at least one gellable component which comprises an aqueous acidic chitosan solution, wherein the chitosan is present in the simulated blood in an amount between about 0.6 to about 2.0 wt. %;
at least one colorant in an amount sufficient to mimic coloration of whole mammalian blood; and
optionally at least one additive selected from the group consisting of viscosity modifiers, tactile agents and scent modifiers, wherein
in response to the gellable simulated liquid blood being brought into contact with a gelling agent, the at least one gellable component is caused to desolubilize, polymerize, complex, precipitate and/or cross-link so as to form a mass of semi-solid or solid material to thereby simulate blood clotting.

24. The simulated blood as in claim 23, wherein the chitosan has a molecular weight of between about 50,000 Da to about 500,000 Da.

25. The simulated blood as in claim 23, wherein the chitosan is autoclaved at temperatures between about 100 to about 150° C., at pressures of between about 5 to about 25 psi and a time of between about 1 minute to about 90 minutes.

26. The simulated blood as in claim 23, wherein the chitosan has a percent deacetylation value (% DA) of at least about 70%.

27. The simulated blood as in claim 23, wherein the aqueous acidic chitosan solution has a pH of between about 4 to about 6.

28. The simulated blood as in claim 23, which comprises a liquid solution of sodium alginate.

29. A simulated hemostatic dressing which comprises:
a fabric substrate; and
a simulated hemostatic component comprising a gelling agent carried by the fabric substrate, wherein
the gelling agent is present in an amount between about 10 wt. % to about 80 wt. %, based on the weight of the fabric substrate; and wherein
the gelling agent is at least one compound selected from the group consisting of sodium tripolyphosphate (NaTPP), calcium salts, β-glycerophospate, sodium bicarbonate, sodium carbonate, sodium citrate, citric acid, and Rose Bengal, and wherein
the gelling agent causes gelling of a simulated blood component comprising a gellable component comprising chitosan and/or alginate by causing the gellable component to desolubilize, polymerize, complex, precipitate and/or cross-link so as to form a semi-solid or solid mass of the gellable component in response to physical contact between the simulated blood component and the gelling agent thereby simulating clotting of natural whole blood.

30. A method of training medical responders to treat wound hemorrhage comprising: (a) providing the medical training kit of claim 1; (b) causing the simulated liquid blood of the medical training kit to flow into a simulated wound; and (c) applying the simulated hemostatic component of the medical training kit to the wound to thereby cause the gelling agent thereof to come into contact with the gellable component of the simulated blood and thereby cause the gelling agent to interact with the gellable component to form a mass of semi-solid or solid material thereby simulating blood clotting.

31. The method as in claim 30, wherein the simulated hemostatic component is in particulate or liquid form.

32. The method as in claim 30, wherein the simulated hemostatic component is a powder, and wherein step (c) comprises applying the powder directly to the simulated wound to cause the powder to contact the simulated blood.

33. The method as in claim 30, wherein the simulated hemostatic component comprises a carrier for the gelling agent selected from the group consisting of a liquid, fabric, sponge or pouch.

34. The method as in claim 30, wherein the simulated hemostatic component comprises a simulated hemostatic dressing which includes a fabric substrate carrying the gelling agent, and wherein step (c) comprises applying the simulated hemostatic dressing to the wound to cause the simulated blood to contact the gelling agent carried by the fabric substrate.

35. The method as in claim 30, wherein the simulated blood component is an aqueous acidic solution comprising chitosan as the gellable component, and wherein the hemostatic component comprises sodium tripolyphosphate (NaTPP).

36. The method as in claim 35, wherein the chitosan is present in the simulated blood component in an amount between about 0.6 to about 2.0 wt. %.

37. The method as in claim 35, wherein the chitosan has a molecular weight of between about 50,000 Da to about 500,000 Da.

38. The method as in claim 35, wherein the chitosan is autoclaved at temperatures between about 100 to about 150°

C., at pressures of between about 5 to about 25 psi and a time of between about 1 minute to about 90 minutes.

39. The method as in claim 35, wherein the chitosan has a percent deacetylation value (% DA) of at least about 70%.

40. The method as in claim 30, wherein the simulated blood component is an aqueous solution comprising sodium alginate as the gellable component, and wherein the simulated hemostatic component comprises calcium chloride.

41. The method as in claim 40, wherein the sodium alginate is present in the simulated blood formulation in an amount between about 0.05 to about 2.0 wt. %.

42. The method as in claim 35 or 40, wherein the simulated blood component comprises at least one colorant in an amount sufficient to mimic coloration of whole mammalian blood.

43. The method as in claim 35 or 40, wherein the simulated blood component comprises at least one additive selected from the group consisting of viscosity modifiers and tactile agents.

44. The method as in claim 43, wherein the simulated blood component comprises a cellulosic material as a viscosity modifier.

45. The method as in claim 43, wherein the simulated blood component comprises glycerol as a tactile agent.

* * * * *